(12) United States Patent
Maertens et al.

(10) Patent No.: US 6,670,114 B1
(45) Date of Patent: Dec. 30, 2003

(54) HOST DERIVED PROTEINS BINDING HCV: MEDICAL, DIAGNOSTIC AND PURIFICATION USE

(75) Inventors: Geert Maertens, Bruges (BE); Erik Depla, Destelbergen (BE)

(73) Assignee: N.V. Innogenetics, Ghent (BE)

(*) Notice: Subject to any disclaimer, the term of this patent is extended or adjusted under 35 U.S.C. 154(b) by 0 days.

(21) Appl. No.: 09/564,951

(22) Filed: May 5, 2000

Related U.S. Application Data

(63) Continuation of application No. PCT/EP98/07107, filed on Nov. 6, 1998.

(30) Foreign Application Priority Data

Nov. 6, 1997 (EP) .............................. 97870178

(51) Int. Cl.$^7$ ................................. C12Q 1/70
(52) U.S. Cl. ........................ 435/5; 435/7.8; 435/7.93
(58) Field of Search ..................... 435/5, 7.8, 7.93

(56) References Cited

U.S. PATENT DOCUMENTS

| | | | | |
|---|---|---|---|---|
| 5,180,679 A | * | 1/1993 | Schmidtberger | ............ 436/517 |
| 5,187,068 A | * | 2/1993 | Luca | .......................... 435/11 |
| 5,206,086 A | * | 4/1993 | Sparks et al. | ............... 428/403 |

FOREIGN PATENT DOCUMENTS

| | | |
|---|---|---|
| DE | 42 06 574 c | 8/1993 |
| WO | WO 94/01554 A | 1/1994 |
| WO | WO 96/04385 | 2/1996 |

OTHER PUBLICATIONS

Thomssen et al., Association of hepatitis C virus in human sera with beta–lipoprotein. Med. Microbiol. Immunol. 181:293–300, 1992.*
Agnello et al., Hepatitis C virus and other Flaviviridae viruses enter cells via low density lipoprotein receptor. Proc. Natl. Acad. Sci. USA 96(22):12766–12771, 1999.*
Sato et al., Association of Circulating Hepatitis G Virus with Lipoproteins for a Lack of Binding with Antibodies. Biochemical an Biophysical Research Communications 229:719–725, 1996.*
Biochemistry, $3^{rd}$ edition of 1988 by L. Stryer, Fig. 23–18.
Monazahian et al. 1995, Abstract C84; $5^{th}$ Int. Symposium on HCV and related viruses; Australia.
Monazahian et al. Med Microbiol Immunol (2000) 188:177–184.
Melki et al, "Interaction Between Tubulin and the Viral Matrix Protein of Vesicular Stomatitis Virus: Possible Implications in the Viral Cytopathic Effect", *VIROLOGY*, vol. 202, 1994, pp. 339–347.
Depla et al, "Interaction of HCV Envelope with Host Tubulin" *HEPATOLOGY*, vol. 28, No. 4 Part 2, Oct. 1998, p. 272A.

* cited by examiner

*Primary Examiner*—Donna C. Wortman
(74) *Attorney, Agent, or Firm*—Nixon & Vanderhye

(57) ABSTRACT

The finding that the human proteins annexin V, tubulin and apolipoprotein B bind to the hepatitis C virus envelope proteins E1 and/or E2 and the usage of these human proteins to diagnose and treat an infection with hepatitis C virus are described. The usage of the latter proteins to enrich HCV envelope proteins and molecules which inhibit binding of HCV to these human proteins, as well as vaccines employing the E1 and/or E2 binding domains are also disclosed.

13 Claims, 14 Drawing Sheets

Figure 3:
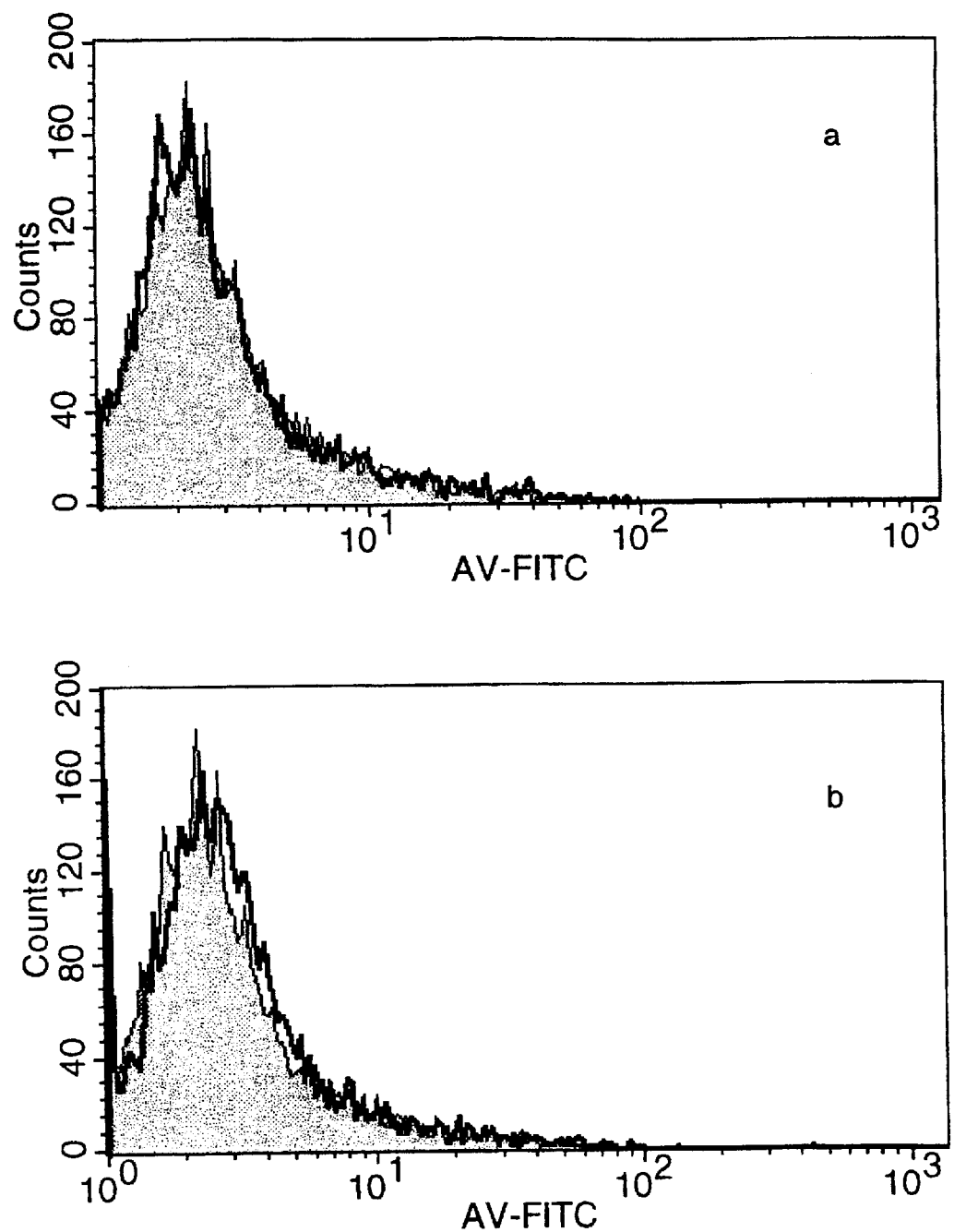

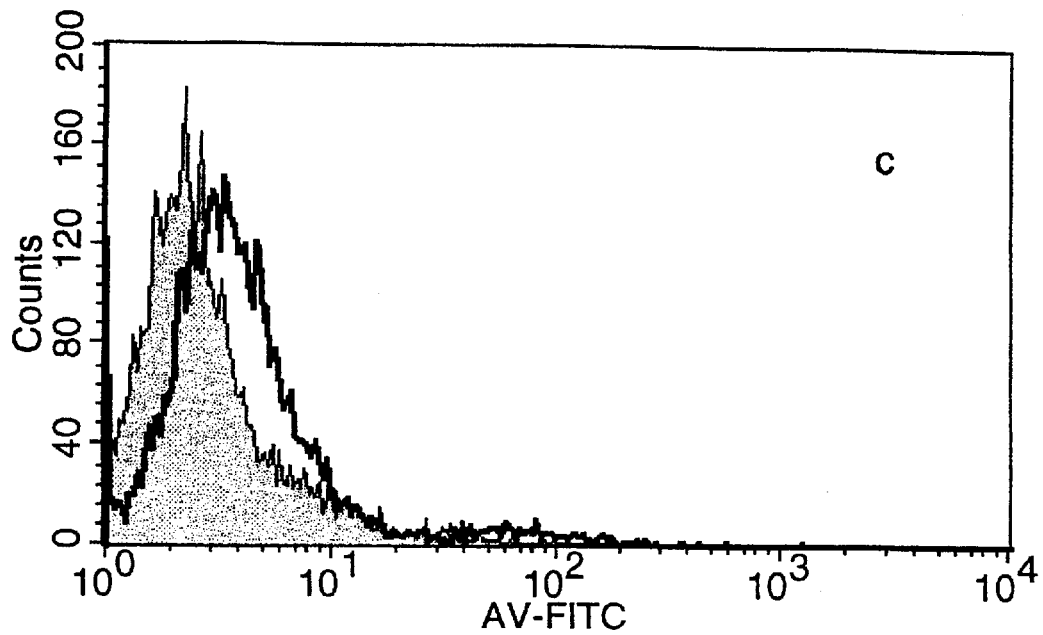
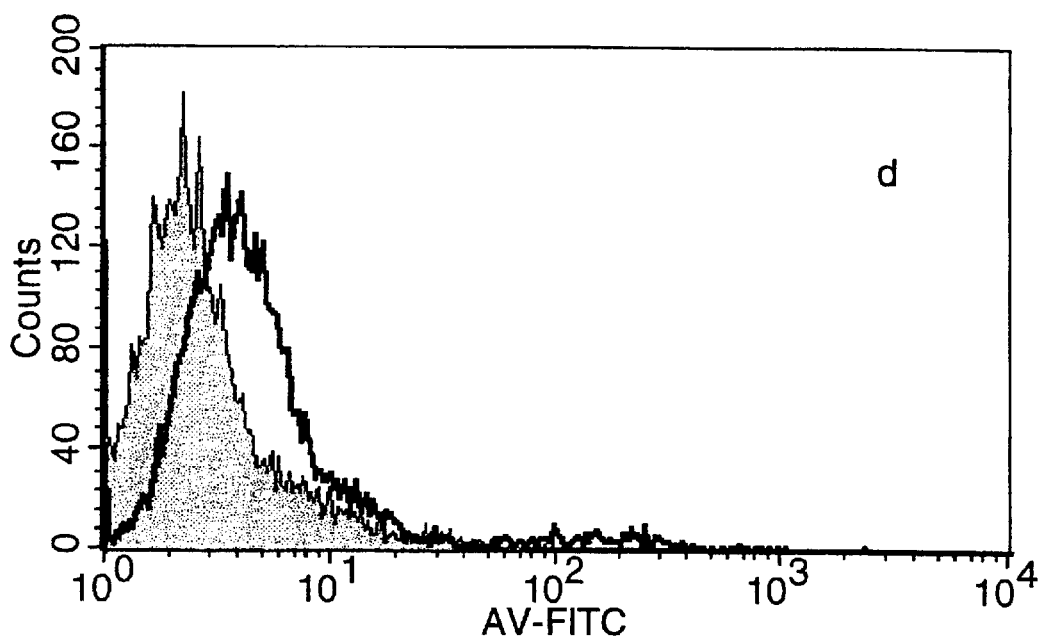
Figure 3 – cont'd 1

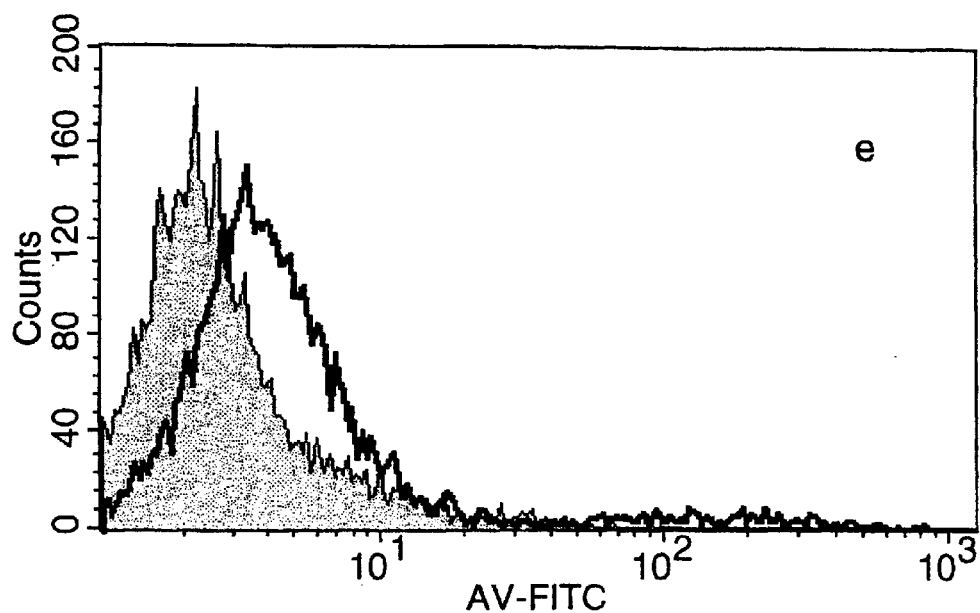
Figure 3 – cont'd 2

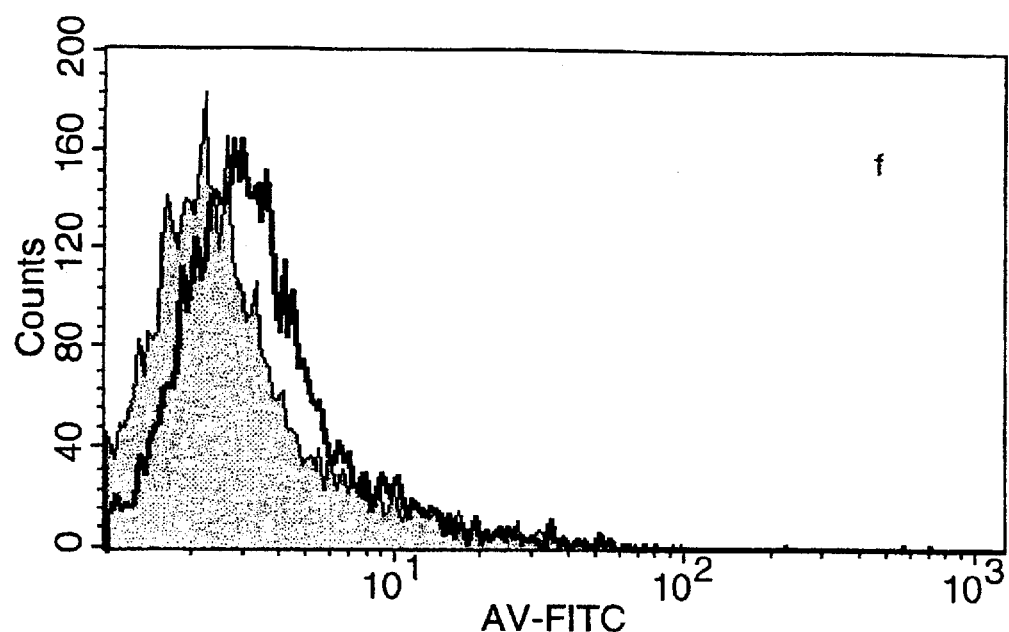
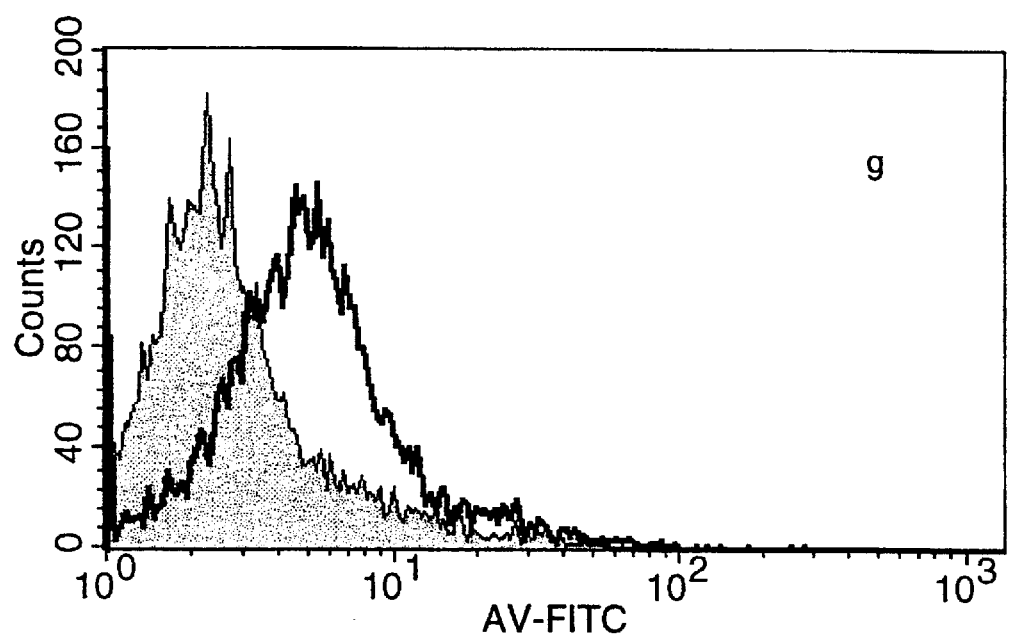
Figure 3 – cont'd 3

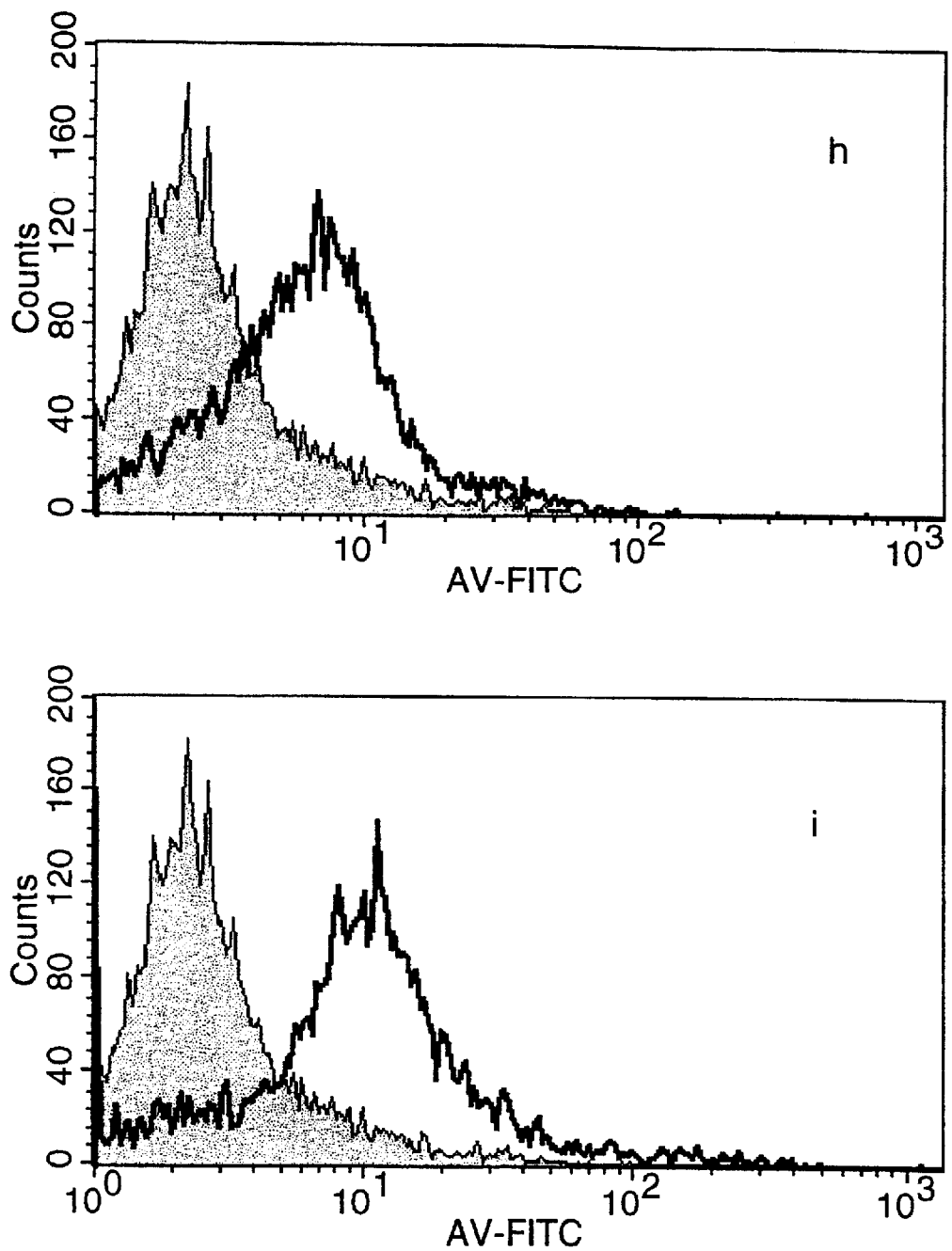
Figure 3 - cont'd 4

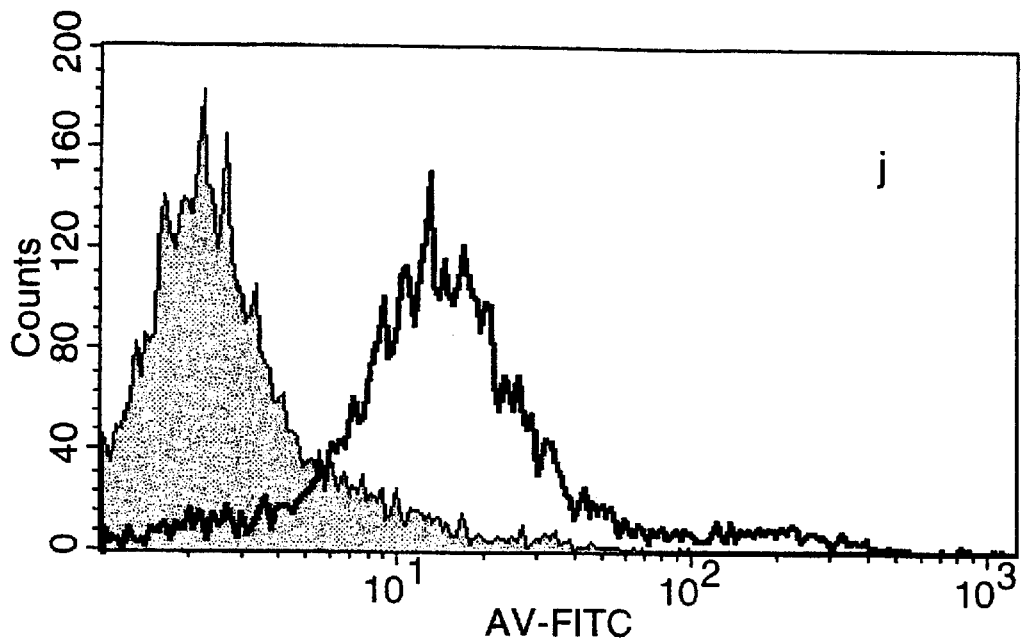
Figure 3 - cont'd 5

Figure 6:
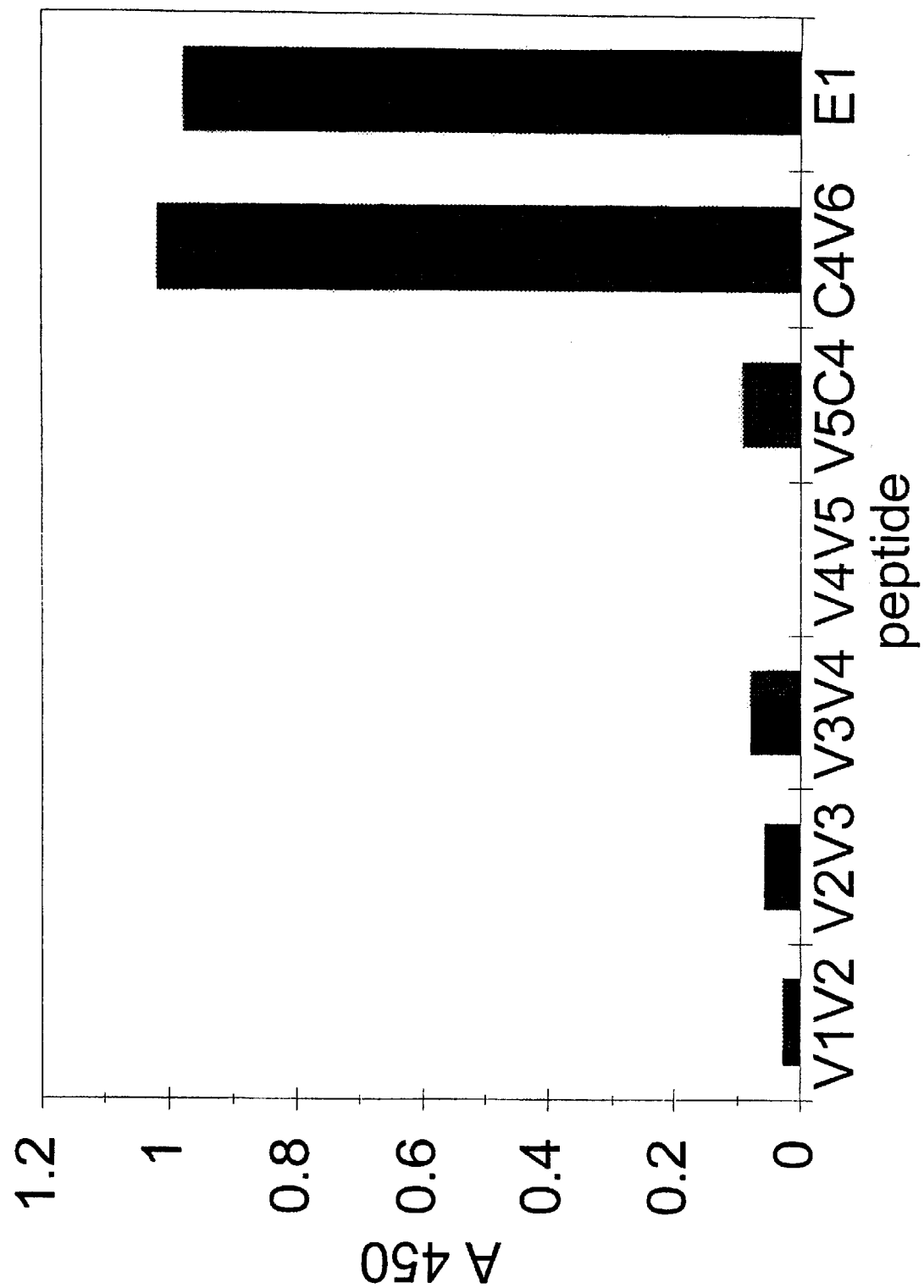

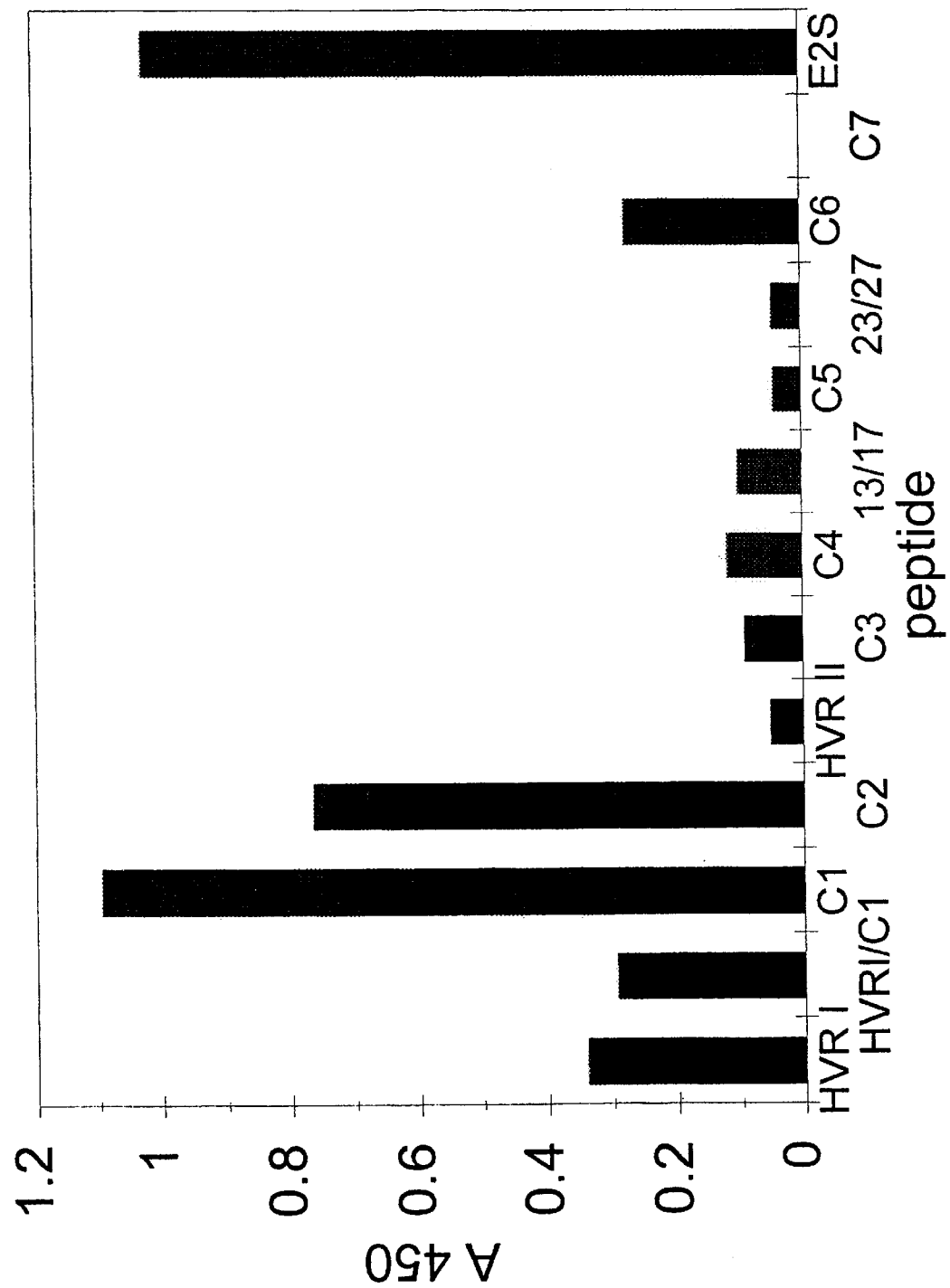
Figure 6 – cont'd

HOST DERIVED PROTEINS BINDING HCV: MEDICAL, DIAGNOSTIC AND PURIFICATION USE

This is a continuation of PCT application PCT/EP98/07107, filed Nov. 6, 1998, the entire content of which is hereby incorporated by reference in this application.

FIELD OF THE INVENTION

The present invention is based on the development of an efficient infection system for HCV, and on the finding that the human proteins annexin V, tubulin and apolipoprotein B bind to the hepatitis C virus envelope proteins E1 and/or E2 and concerns the usage of these human proteins to diagnose and treat an infection with hepatitis C virus. The present invention also relates to the usage of the latter proteins to enrich HCV envelope proteins and to molecules which inhibit binding of HCV to these human proteins, as well as vaccines employing the E1 and/or E2 binding domains.

BACKGROUND OF THE INVENTION

Hepatitis C virus (HCV) infection is a major health problem in both developed and developing countries. It is estimated that about 1 to 5% of the world population is affected by the virus, amounting up to 175 million chronic infections worldwide. HCV infection appears to be the most important cause of transfusion-associated hepatitis and frequently progresses to chronic liver damage. Moreover, there is evidence implicating HCV in induction of hepatocellular carcinoma. Consequently, the demand for reliable diagnostic methods and effective therapeutic measures is high. Also sensitive and specific screening methods for HCV-contaminated blood-products and improved methods to culture HCV are needed.

HCV is a positive stranded RNA virus of about 9,8 kilobases which code for at least three structural and at least six non-structural proteins. The structural proteins have not yet been functionally assigned, but are thought to consist of a single core protein and two envelope proteins E1 and E2. The E1 protein consists of 192 amino acids and contains 5 to 6 N-glycosylation sites, depending on the HCV genotype, whereas the E2 protein consists of 363 to 370 amino acids and contains up to 11 N-glycosylation sites, depending on the HCV genotype (for review see Maertens and Stuyver, 1997). The latter envelope proteins have been produced by recombinant techniques using *Escherichia coli*, baculovirus, yeast and mammalian expression systems. The usage of an expression system in higher eukaryotes and especially in mammalian cell culture leads to envelope proteins of superior quality, i.e. they are effectively recognized by antibodies recovered from HCV patients (Maertens et al., 1994, de Martynoff et al., 1996).

Standardized infections of live viruses are a prerequisite for studying the binding parameters of HCV to eukaryotic cells. Controllable infection of eukaryotic cells by HCV, however, poses a problem. As a partial solution to this problem, a Daudi cell line was selected, which was supporting productive infection for HCV (Shimizu et al., 1996). However, the inocula for infection gave variable results in Molt-4 cells and even in Daudi cells. Consequently, comparative studies, e.g. on the development of drugs interfering with the interaction of HCV with its target eukaryotic cell are troublesome. Therefore, there is an urgent need for a protocol, which guarantees efficient and reliable infections of eukaryotic cells by HCV.

The HCV envelope proteins E1 and E2 interact with each other to form hetero-oligomeric complexes. Although the exact role of these HCV envelope proteins has not been elucidated yet, it has been suggested that they are responsible for binding of the virus to target cells. Indeed, binding of E2, mostly involving the highly variable amino terminus of E2 (i.e. the hyper variable region I), to target cells has been documented by several authors (Farci et al., 1996; Shimizu et al., 1994; Zibert et al., 1995 and Rosa et al., 1996). Furthermore, several host proteins have been shown to bind to one or both envelope proteins. For example, the chaperone protein calnexin has been shown to interact with both E1 and E2 and, by doing so, to support correct folding of both envelope proteins (Deleersnyder et al., 1997). Also lactoferrin, a protein mainly found in milk, has been demonstrated to bind to both envelope proteins (Yi et al., 1997b). However, the role of this interaction is unclear. A 24 kDa plasma membrane protein has been described which binds specifically to E2 (WO 97/09349 to Abrignani). The latter protein has been suggested to be a cellular receptor for HCV. Also the mannose receptor on hepatic endothelial cells and macrophages and the asialoglycoprotein receptor on hepatocytes have been suggested to function as receptors for HCV via the E1 and E2 proteins (WO92/08734 to Raiston et al.). In addition, RNA of HCV in serum of patients is often found associated with the LDL-fraction of serum (Thomsson et al., 1992 & 1993; Agnello et al., 1996 &1997). The nature of this finding, has not been unravelled yet.

Taken together, several HCV-binding proteins have been described in the literature. However, no prior art exists regarding the binding of the human proteins annexin V, apolipoproteinB, or tubulin to the hepatitis C virus envelope proteins E1 and/or E2. Neither has the interaction between HCV and LDL been further unravelled with regard to the components of LDL involved, ie protein, lipid or sugar, nor with regard to the regions of the HCV proteins involved, ie the envelope proteins E1 and/or E2.

Annexin V (also termed endonexin II, placental anticoagulant protein, PP4 or lipocortin V) is a member of the family of structurally closely related $Ca^{2+}$-dependent phospholipid-binding proteins, known as annexins, which have molecular weights between 32 and 67 kDa (Klee, 1988; Zaks & Creutz, 1990). Annexin V is found in various tissues such as liver, spleen, lung, intestine and placenta (Walker et al., 1990). The protein has been described to bind, in a $Ca^{2+}$-dependent manner, to placental membranes (Haigler et al., 1987) and to inhibit blood coagulation (Grundman et al., 1988) and phospholipase A2 activity in vitro (Pepinsky et al., 1988). Other investigators have demonstrated that annexin V behaves like an integral membrane protein and forms calcium-selective cation channels (Rojas et al., 1990; Bianchi et al., 1992).

We have recently shown that annexin V, present on human liver plasma membranes, specifically binds to "small" HBsAg, one of the envelope glycoproteins of hepatitis B virus (HBV), in a $Ca^{24+}$-dependent manner (Hertogs et al., 1993; WO 94/01554). The receptor-ligand relationship between HBsAg and annexin V is further supported by the observation that rabbits, immunized with native human liver annexin V or recombinant annexin V, or chickens, immunized with $F(ab')_2$-fragments of rabbit anti-annexin V IgG, spontaneously develop anti-idiotypic antibodies (Ab2) which specifically recognize HBsAg (Hertogs et al., 1994). Since HCV is an RNA virus belonging to the family of flaviviridae, and HBV is a DNA virus belonging to the family of hepadnaviruses, the binding of annexin to E1 or E2 of HCV was completely unexpected.

Tubulin is a soluble protein found in most eukaryotic cells and is the principal protein subunit of microtubules in the cell. Microtubules are the principal components of mitotic and meiotic spindles and of the axons of neuronal cells. Microtubules also participate in several aspects of intracellular transport, in maintenance of various cell surface properties such as receptor capping and they establish overall cell shape and internal cytoplasmic architecture. Tubulin extracted from neurons is a dimer of about 100 kDa. each dimer being composed of two polypeptides α-tubulin (50 kDa) and β-tubulin (50 kDa), which have closely related amino acid sequences (Alberts et al., 1983).

Tubulin has been implicated in the transcription of Sendai virus (Takagi et al, 1996) and has been shown to be involved during intracellular transport of herpes simplex virus type 1 (Hammonds et al., 1996) and tobacco mosaic virus (McLean et al., 1995). Tubulin appears also to interact with the matrix protein of vesicular stomatitis virus (Melki et al., 1994).

Apolipoprotein B (ApoB) represents the main protein component of the low-density lipoproteins (LDL). Besides its lipid-carrier property apoB is involved in the secretion into the plasma of newly synthesized triglyceride-rich particles and also as a ligand for the high-affinity membrane receptor responsible for the uptake and degradation of LDL (Scanu, 1987). Although E1has been implied in binding to LDL (Monazahian et al., 1995), the specific domains of E1 directly interacting have never been elucidated. Moreover, it is unclear whether the binding of E1 to LDL is mediated through the lipid or sugar component or any of the protein components of LDL.

Hence, no prior art exists which demonstrates or suggests the binding of the human proteins annexin V, tubulin or apoB to the hepatitis C virus envelope proteins E1 and/or E2 leading to the development of reliable methodological tools to diagnose HCV and effective therapeutic agents to treat or prevent HCV infections. Although annexins and tubulin have been described to interact with other viruses, there is no evidence to suppose an interaction with HCV, especially since none of the described viruses belongs to the flavivirus or pestivirus families.

AIMS OF THE INVENTION

It is clear from the literature that there is an urgent need to develop reliable diagnostic methods, reliable vaccines, and effective therapeutic and prophylactic agents for HCV. In addition, sensitive and specific screening methods of HCV-contaminated blood-products and improved methods to culture HCV are needed as well as reliable infection protocols. Knowing which human proteins bind to HCV, and function as putative receptor for HCV, may help in designing efficient diagnostic tools and therapeutic agents. In this regard, the present invention is based on the surprising finding that the human proteins annexin V, tubulin and apolipoprotein B bind to HCV via its envelope complex which is composed of the E1 and E2 proteins.

Therefore, the present invention aims at providing a human protein, or a functionally equivalent variant or fragment thereof, chosen from the group consisting of annexin V, tubulin and apolipoprotein B for use in the preparation of:
  a composition to treat an infection with HCV, or
  a method to diagnose an infection with HCV, or
  a method to purify HCV proteins, or
  a method for propagating HCV in cell culture.

More specifically, the present invention aims at providing a protein as defined above, wherein said protein, or a functionally equivalent variant or fragment thereof, binds to HCV, and more preferably to the envelope proteins E1 and/or E2 of HCV.

In addition, the present invention aims at providing a protein as defined above, wherein said annexin V, or a functionally equivalent variant or fragment thereof, binds to the amino acids 307–326 of E1 and/or the amino acids 413–467 of E2.

In addition, the present invention aims at providing a protein as defined above, wherein said tubulin, or a functionally equivalent variant or fragment thereof, binds to the amino acids 192–326 of E1 and/or the amino acids 384–673 of E2.

In addition, the present invention aims at providing a protein as defined above, wherein said apolipoprotein B, or a functionally equivalent variant or fragment thereof, binds to the amino acids 192–263 and/or the amino acids 288–326 of E1.

The present invention aims also at providing a composition comprising an HCV E1 and/or E2 peptide, or a functionally equivalent, or variant thereof, which contains a binding domain for a human protein as defined above, and said composition can be used prophylactically; or therapeutically. Such a composition can be used to generate antibodies interfering directly with the viral life cycle and will therefore be highly potent. Moreover, the peptide or its functionally equivalent can be used as a drug competing with the natural interaction and thus interfering directly with the viral life cycle.

It is also an aim of the present invention to provide a composition comprising a human protein as described above, or any functionally equivalent variant or fragment thereof, and a carrier for use to treat an infection with HCV. A composition which targets essential functions in the life cycle of HCV and may be highly efficient and is expected to be cross-protective against all HCV genotypes.

It should be clear that the interactions between host proteins and HCV envelope proteins may not be limited to the examples disclosed here (i.e. tubulin, annexin V and apolipoprotein B).

It is therefore an aim of the present invention to provide any host protein, or a functionally equivalent variant or fragment thereof, which interacts with HCV envelope proteins and which can be used in the preparation of a drug to treat an infection with HCV, or, a method to diagnose an infection with HCV, or, a method to purify HCV proteins, or, a method to propagate HCV in culture.

The present invention further aims at providing a method for diagnosing exposure to or infection by HCV comprising contacting HCV within a sample of body fluid with a host protein as described above, or a functionally equivalent variant or fragment thereof, and determining the binding of HCV within a sample of body fluid with a host protein as described above, or a functionally equivalent variant or fragment thereof. For example, apoB, tubulins and/or annexins may be employed to capture and/or detect HCV particles.

Moreover, the present invention aims at providing a method for purifying HCV envelope proteins comprising contacting a composition containing HCV envelope proteins with a human protein as described above, or a functionally equivalent variant or fragment thereof, and isolating the portion of the composition which binds to said protein as described above, or a functionally equivalent variant or fragment thereof.

The present invention also aims at providing an assay kit for detecting the presence of HCV comprising a solid support, a human protein as described above or a functionally equivalent variant or fragment thereof, and appropriate markers which allow to determine the complexes formed between HCV in sample of body fluid with a human protein as described above, or a functionally equivalent variant or fragment thereof.

In addition, the present invention aims at providing a method for propagating HCV in cell culture comprising providing a cell that over-expresses a human protein as described above, or a functionally equivalent variant or fragment thereof, infecting the cell with HCV, and culturing the infected cell.

Furthermore, the present invention aims at providing a method for reducing or eliminating the presence of HCV in plasma, serum, or other biological liquids which method comprises contacting said biological liquid with a human protein as described above, or a functionally equivalent variant or fragment thereof, and separating said biological liquid from said protein as described above, or a functionally equivalent variant or fragment thereof.

Moreover, the present invention aims at providing a method to determine anti-HCV antibodies in plasma, serum, or other biological liquids which method comprises allowing competitive binding between antibodies in the biological liquid and a known amount of HCV envelope protein for binding to a human protein as described above or a functionally equivalent variant or fragment thereof, and determining the amount of the HCV envelope protein bound.

The present invention also aims at providing a method to screen for molecules which modulate the binding between HCV and a human protein as described above, or a functionally equivalent variant or fragment thereof.

The present invention aims also at providing a composition comprising a molecule which modulates the binding between HCV and a human protein as described above, or a functionally equivalent variant or fragment thereof.

The present invention aims also at providing an in vitro infection method of eukaryotic cells for HCV by using purified HCV particles. More particularly, purifying HCV particles by ultra centrifugation of a solution containing said HCV particles. More particularly, purifying HCV particles by ultra centrifugation of a body fluid containing said HCV particles. More particularly, infecting Daudi, Molt, HepG2, or any B-, T-, macrophage, hepatocyte or hepatome cell line in vitro with said purified HCV particles.

The present invention aims also at characterizing said purified HCV particles for the content of E1 and/or E2 proteins. Moreover, the present invention aims also at characterizing said purified HCV particles for the content of antibodies against E1 and/or E2. Moreover, the present invention aims also at characterizing said purified HCV particles for the content of LDL. Moreover, the present invention aims also at characterizing said purified HCV particles for the content of apolipoprotein B.

The present invention aims also at providing an in vitro infection system to be used for screening for molecules which modulate the binding between HCV and eukaryotic cells.

In addition, the present invention aims at providing an in vitro infection system to be used for diagnosing exposure to or infection by HCV comprising purifying HCV particles as described above, infecting host cells as described above, and determining the multiplicity of infection.

Finally, the present invention aims at providing isolated HCV E1 and/or E2 peptides as defined by SEQ ID NO 1 to 6 (Table 4), or any fragment thereof, wherein said sequence binds to annexin V, tubulin and/or apolipoprotein B.

All the aims of the present invention are considered to have been met by the embodiments as set out below.

BRIEF DESCRIPTION OF TABLES AND DRAWINGS

Table 1 provides the characterization of sera (42 and 46, "before") containing HCV and the inocula (42 and 46, "after") derived thereof ("E1/E2"=levels of E1 and/or E2 proteins; "pos"=positive; "neg"=negative; "nd"=not determined; "genotype"=genotype of HCV).

Table 2 shows the levels of HCV-RNA measured after infecting Daudi B cells using the inocula 42 and 46 as characterized in Table 1 ("CF"=cell fraction; "SN"=supernatant; "−"=negative; "+"=positive after a second (nested) round of PCR; "+(+)"=weakly positive after a first round of PCR and confirmed after nested PCR; "++"=positive after 1 round of PCR).

Table 3 demonstrates the results of FACS analysis for bindings of E1s or E2s to different cell lines. ("−"=no binding; "(+)"=weak binding (S(ignal)/N(oise): 1-2); "+"=clear binding (S/N 2-3); "++"=strong binding (S/N >3); nd=not determined).

Table 4 lists amino acid sequences of E1 and E2 protein fragments and the corresponding SEQ ID NOs, as used in this invention.

FIG. 1 shows the determination of the E1/E2 proteins in purified inocula derived from human sera 42 and 46.

FIG. 2 shows binding2 of the envelope proteins E1s, E1s Δbam and E2s to solid phase LDL (A) or apolipoprotein B100 (B) which are coated on a microtiterplate. Binding of the biotinylated envelope proteins was detected by streptavidin-peroxidase.

FIGS. 3*a–j* shows the concentration dependency of binding of biotinylated E1s and biotinylated E2s to Daudi cells. Binding, was evaluated by FACS analysis using streptavidin-FITC. Figures a–e show binding of E1s while figures f–j show binding of E2s. On each individual figure the result of the control experiment (no envelope protein present) is shown as a thin line with the shaded area. Figures a and f, b and g, c and h, d and l, e and j show the binding of respectively 1, 2, 5. 10 and 20 $\mu$g of E1s or E2s (bold line without shading).

FIG. 4 shows an SDS-PAGE from the proteins eluted a the third elution (alkaline/detergent) step from an E2 affinity column to which a total lysate of Daudi cells was allowed to bind. Lane 1 and 3 represent molecular weight markers (from top to bottom, 113, 67, 45, 29, 18, 12 kDa) while lane 2 shows the eluted material. Note the bands in lane 2 at 55 kDa (specific for E2 or E1 affinity columns only) and at 70 kDa (not specific since it is also recovered from an affinity column without E1 or E2).

FIG. 5 shows a Western blot using specific monoclonal antibodies (Sigma Chemical Co, St. Louis, Mo.) against tubulin. Lane 1: tubulin standard (Sigma); Lanes 2 and 5: molecular weight markers; Lane 3: elution 3 from an E1 column; lane 4: elution 3 from an E2 column.

FIG. 6 shows binding of annexin V, labelled with peroxidase, E1, E2, and peptides derived of E1 or E2 (6A and 6B, respectively), which were all biotinylated and adsorbed to streptavidin-coated microtiterplates.

FIGS. 7A–7B shows the Western blot analysis of immunoprecipitation experiments of E1/tubulin (right; Lane 1: immunoprecipitation of E1/tubulin complex with anti-tubulin; lane 2: markers (175, 83, 62, 47, 32), lane 3, negative control lane: E1 precipitation with anti-tubulin without addition of tubulin, lane 4: positive control lane containing 100 ng purified E1), and E2/tubulin (left; Lane 1: immunoprecipitation of E2/tubulin complex with anti-tubulin; lane 2: markers (175, 83, 62, 47, 32), lane 3, negative control lane: E2 precipitation with anti-tubulin without addition of tubulin, lane 4: positive control lane containing 100 ng purified E2 markers).

DETAILED DESCRIPTION OF THE INVENTION

The invention described herein draws on previously published work and pending patent applications. By way of example, such work consists of scientific papers, patents or pending patent applications. All these publications and applications, cited previously or below are hereby incorporated by reference.

The present invention is based on the finding that the HCV envelope proteins E1 and/or E2 bind to human proteins. The term "bind" indicates that the E1 and/or E2 proteins are physically connected to, and interact with, the human proteins. In this regard, the term "binding domain" refers to a specific amino acid stretch of an E1 and/or E2 protein which is able to bind the human proteins. Binding of the viral proteins to the human proteins can be demonstrated by any method or assay known in the art such as fluorescence flow cytometry, binding-, ELISA- and RIA-type assays or competition assays (see Examples section and Hertogs et al., 1993).

The HCV envelope proteins E1 and E2 relate to the well-characterized HCV proteins as described previously (see Background of the invention section) and in Major and Feinstone (1997) and WO92/08734 to Ralston et al., or fragments thereof, or functionally equivalent variants. It should be clear that said fragments and functionally equivalent variants intrinsically have the property to bind a human protein as described below. Moreover, it should be clear that a functionally equivalent variant of an HCV E1 and/or E2 protein relates to any E1 and/or E2 envelope protein of all HCV genotypes, and HCV-related viruses such as HGV, GBV-A and GBV-B. These proteins can be obtained by the ones described in WO96/04385 to Maertens et al. and in the Examples section.

The proteins used in this invention are derived from a HCV genotype 1b sequence and have been described by de Martynoff et al. (1996). Both E1 and E2 are produced by mammalian cells as truncated proteins and will be referred to as E1s (aa 192–326) and E2s (384–673).

The term "human protein" relates to any human protein (i.e. any of numerous naturally occurring extremely complex combinations of amino acids), or fragments thereof (i.e. simpler combinations of fewer amino acids, such as polypeptides and peptides, derived from said proteins), which bind to the HCV envelope proteins E1 and/or E2. These human proteins can be extracted from any human cell or cell line by any method known in the art such as the ones described in WO/9709349 to Abrignani and the Examples section of the present application and can be characterized and sequenced by any method known in the art. Consequently, the latter proteins can also be produced by means of recombinant DNA techniques such as described by Maniatis et al. (1982). Polypeptides and peptides derived from said proteins, as herein described, can be prepared by any method known in the art such as classical chemical synthesis, as described by Houbenweyl (1974) and Atherton & Shepard (1989), or by means of recombinant DNA techniques by Maniatis et al. (1982). It should be clear that the terms "polypeptide" and "peptide" refer to a polymer of amino acids (aa) which comprises less aa in its sequence than said proteins and do not refer to, nor do they exclude, post-translational modifications of the polypeptides and peptides such as glycosylation, acetylation, phosphorylation, modifications with fatty acids and the like. Included within the definition are, for example, polypeptides and peptides containing one or more analogues of an aa (including unnatural aa's), polypeptides and peptides with substituted linkages, mutated versions or natural sequence variations of the polypeptides and peptides, polypeptides and peptides containing disulphide bounds between cysteine residues, as well as other modifications known in the art.

More specifically, the present invention relates to the well known human proteins annexin V, tubulin and apolipoprotein B (see Background of the invention section), or a functionally equivalent or fragment of annexin V, tubulin or apolipoprotein B, which can be used in a composition to treat an infection with HCV, or, a method to diagnose an infection with HCV, or, a method to purify HCV proteins, or a method for propagating HCV in cell culture. It should be clear that the term "a functionally equivalent" relates to any obvious equivalent of annexin V, tubulin and apolipoprotein B, such as other members of the annexin family of proteins or tubulin-alpha or -beta (see Background of the invention section), which binds HCV. The term "a functionally fragment" relates to any polypeptide or peptide as defined above which binds HCV. Furthermore, the present invention relates to the binding of the proteins annexin V, tubulin and apoB, or a functionally equivalent or fragment of annexin V, tubulin and apolipoprotein B, to HCV, and in particular to HCV envelope proteins E1 and E2.

More specifically, the present invention relates to the binding of tubulin to the amino acids 192–326 of E1 and the amino acids 384–673 of E2.

The present invention also relates to the binding of annexin V to the amino acids 307–326 of E1 and the amino acids 413–467 of E2.

The present invention also relates to the binding of apolipoprotein B to the amino acids 192–263 and the amino acids 288–326 of E1.

The amino acid regions of E1 and E2 refer to the aa numbering of a typical genotype 1b sequence with an aa numbering commencing from the initiation methionine of the HCV polyprotein which is described in Maertens and Stuyver (1997).

The present invention also pertains to a composition comprising a protein, or a functionally equivalent or variant thereof, as defined above, and a carrier for use to treat an infection with HCV. The terms a composition to treat an infection with HCV relates to any protein, polypeptide or peptide as defined above which prevents, ameliorates or cures an infection with HCV or a closely related infection with other non-A, non-B hepatitis viruses such as HGV, GBV-A, GBV-B, or other related viruses. It should also be clear that the term; "an infection with HCV" implies an infection with any genotype or any mixture of genotypes of HCV. More specifically, the terms a composition to treat an infection with HCV relates to a pharmaceutical composition or medicament (both terms can be used interchangeably) comprising a protein, polypeptide or peptide as described herein and a pharmaceutically acceptable carrier or excipient (both terms can be used interchangeably) to treat an infection with HCV. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The "medicament" may be administered by any suitable method within the knowledge of the skilled man.

The preferred route of administration is parenterally. In parental administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the protein, polypeptide or peptide of the present invention is given at a dose between 1 µg/kg and 10 mg/kg, more preferably between 10 µg/kg and 5 mg/kg, most preferably between 0.1 and 2 mg/kg. Preferably, it is given as a bolus dose. Continuous infusion may also be used. If so, the medicament may be infused at a dose between 5 and 20 µg/kg/minute, more preferably between 7 and 15 µg/kg/minute.

The present invention further concerns a method for diagnosing exposure to or infection by HCV comprising contacting HCV within a sample of body fluid with a protein as described above, or a functionally equivalent variant or fragment thereof as described above, and determining the binding of HCV within a sample of body fluid with a protein as described above, or a functionally equivalent variant or fragment thereof as described above. As used herein, the term "a method for diagnosing" refers to any immunoassay known in the art such as assays which utilize biotin and avidin or streptavidin, ELISAs and immunoprecipitation and agglutination assays. A detailed description of these assays is given in WO 96/13590 to Maertens & Stuyver and Current protocols in immunology (1992). The term "body fluid" refers to any fluid obtained from an organism, such as serum, plasma, saliva, gastric secretions, mucus, and the like.

In this regard, the present invention also relates to an assay kit for detecting the presence of HCV comprising a solid support, a protein as described above or a functionally equivalent variant or fragment thereof, and appropriate markers which allow to determine the complexes formed between HCV in sample of body fluid with a protein as described above, or a functionally equivalent variant or fragment thereof. The term "a solid support" refers to any solid support known in the art such as the ones described in Current protocols in immunology. (1992). Similarly, the term "appropriate markers" refers to any marker known in the art (Current protocols in immunology, 1992).

Some biological fluids are used as a source of other products, such as clotting factors, serum albumin, growth hormone, and the like. In such cases it is important that the source biological fluid be free of contamination by viruses such as HCV. Therefore, the present invention also relates to a method for reducing or eliminating the presence of HCV in plasma, serum, or other biological liquids, which method comprises contacting said biological liquid with a protein as described above, or a functionally equivalent variant or fragment thereof, and separating said biological liquid from said protein as described above, or a functionally equivalent variant or fragment thereof. It should be clear that the term "a method for reducing, eliminating or purifying" relates to any method known in the art.

Similarly, it can be important to purify envelope proteins of viruses such as HCV for research purposes or industrial applications. Therefore, the present invention also relates to method for purifying HCV envelope proteins comprising contacting a composition containing HCV envelope proteins with a protein as described above, or a functionally equivalent variant or fragment thereof, and isolating the portion of the composition which binds to said protein as described above, or a functionally equivalent variant or fragment thereof. The term "a composition containing HCV envelope proteins" refers to any biological sample which may contain HCV envelope proteins.

In addition, the present invention concerns a method for propagating HCV in cell culture comprising providing a cell that over-expresses a protein as described above, or a functionally equivalent variant or fragment thereof, infecting the cell with HCV, and culturing the infected cell. In this regard, it should be clear that any method known in the art to transfect a cell, such as the ones described in Current protocols in immunology (1992) with a protein as described above, or a functionally equivalent variant or fragment thereof, can be used. Similarly, any method known in the art to culture the transfected, and/or HCV-infected, cells can be used (Shimizu et al., 1996). The term "over-expresses" refers to host cells which express the proteins and derivatives (i.e. variants and fragments) of the present invention more abundantly (i.e. a greater number of the proteins and derivatives are expressed) in comparison to normal, non-transfected cells.

Moreover, the present invention concerns a method to determine anti-HCV antibodies in plasma, serum, or other biological liquids which method comprises allowing competitive binding between antibodies in the biological liquid and a known amount of HCV envelope protein for binding to a protein as described above or a functionally equivalent variant or fragment thereof, and determining the amount of the HCV envelope protein bound. As used herein, the term "antibody" refers to polyclonal or monoclonal antibodies. The term "monoclonal antibody" refers to an antibody composition having a homogeneous antibody population. The term is not limiting regarding the species or source of the antibody, nor is it intended to be limited by the manner in which it is made. In addition, the term "antibody" also refers to humanized antibodies in which at least a portion of the framework regions of an immunoglobulin are derived from human immunoglobulin sequences and single chain antibodies as described in U.S. Pat. No. 4,946,778 and to fragments of antibodies such as $F_{ab}$, $F_{'(ab)2}$, $F_v$, and other fragments which retain the antigen binding function and specificity of the parental antibody. The term "a method to determine anti-HCV antibodies" refers to any suitable method known in the art.

The present invention also concerns a method to screen for molecules, including but not limited to antibodies, which modulate the binding between HCV and a protein as described above, or a functionally equivalent variant or fragment thereof. As used herein, the term "a method to screen for molecules" refers to any assay known in the art suitable for screening. In particular, the term refers to any immunoassay as described in WO 96/13590. The terms "modulation" or "modulate" as used herein refer to both up regulation (i.e., activation or stimulation (e.g., by agonizing or potentiating)) and down regulation (i.e. inhibition or suppression (e.g., by antagonizing, decreasing or inhibiting) of the binding between HCV and a protein as described above. The term "molecule" refers to any compound, which targets or binds a polypeptide as defined above. The term "molecule" specifically relates to antibodies raised by the host upon vaccination with the above-described HCV peptides (derived from the E1 and E2 envelope proteins and are also named herein "the E1 and E2 binding domains" (see above)) which bind to a protein as defined above. Indeed, the latter HCV peptides can be used in a vaccine or vaccine composition against HCV. Therefore, the present invention concerns a composition comprising an HCV E1 and/or E2 peptide, or a functionally equivalent variant thereof, which contain binding domains for human proteins as described above, and a carrier as described herein, for use to treat or to prevent an infection with HCV. The latter composition, hereafter called "vaccine composition" comprises as an active substance an HCV derived peptide as described above or a combination of HCV-derived peptides as described above for use as a source to vaccinate humans against infection with hepatitis C virus or any mutated strain thereof or any related virus such as HGV, GBV-A or GBV-B. The term "a vaccine composition" relates to an immunogenic composition capable of eliciting protection against HCV, whether partial or complete. The term "as an active substance" relates to the component of the vaccine composition which elicits protection against HCV. An active substance (i.e. the peptides of the present invention) can be used as such, in a biotinylated form (as explained in WO 93/18054) and/or complexed to Neutralite Avidin according to the manufacturer's instruction sheet (Molecular Probes Inc., Eugene, Oreg.). In this regard, it should be clear that a vaccine composition comprises a plasmid vector comprising a nucleotide sequence encoding a polypeptide a modulator operably linked to transcription regulatory elements. As used herein, a "plasmid vector" refers to a nucleic acid molecule capable of transporting another nucleic acid to which it has been linked. Preferred vectors are those capable of autonomous replication and/or expression of nucleic acids to which they have been linked. In general, but not limited to those, plasmid vectors are circular double stranded DNA loops which, in their vector form, are not bound to the chromosome. As used herein, a "nucleotide sequence" refers to polynucleotides such as deoxyribonucleic acid (DNA), and, where appropriate, ribonucleic acid (RNA). The term should also be understood to include, as equivalents, analogs of either RNA or DNA made from nucleotide analogs, and single (sense or antisense) and double-stranded polynucleotides. As used herein, the term "transcription regulatory elements" refers to a nucleotide sequence which contains essential regulatory elements, ie, such that upon introduction into a living vertebrate cell it is able to direct the cellular machinery to produce translation products encoded by the polynucleotide. The term "operably linked" refers to a juxtaposition wherein the components are configured so as to perform their usual function. Thus, transcription regulatory elements operably linked to a nucleotide sequence are capable of effecting the expression of said nucleotide sequence. Those skilled in the art can appreciate that different transcriptional promoters, terminators, carrier vectors or specific gene sequences may be used successfully. It should also be noted that "a vaccine composition" comprises, in addition to an active substance, a suitable excipient, diluent, carrier and/or adjuvant which, by themselves, do not induce the production of antibodies harmful to the individual receiving the composition nor do they elicit protection. Suitable carriers are typically large slowly metabolized macromolecules such as proteins, polysaccharides, polylactic acids, polyglycolic acids, polymeric aa's, aa copolymers and inactive virus particles. Such carriers are well known to those skilled in the art. Preferred adjuvants to enhance effectiveness of the composition include, but are not limited to: aluminium hydroxide, aluminium in combination with 3-0-deacylated monophosphoryl lipid A as described in WO 93/19780. aluminium phosphate as described in WO 93/24148. N-acetyl-muramyl-L-threonyl-D-isoglutamine as described in U.S. Pat. No. 4,606,918, N-acetyl-normuramyl-L-alanyl-D-isoglutamine, N-acetylmuramyl-L-alanyl-D-isoglutamyl-L-alanine2 (1'2'dipalmitoyl-sn-glycero-3-hydroxyphosphoryloxy) ethylamine and RIBl (ImmunoChem Research Inc., Hamilton, Mont.) which contains monophosphoryl lipid A, detoxified endotoxin, trehalose-6,6-dimycolate, and cell wall skeleton (MPL+TDM+CWS) in a 2% squalene/Tween 80 emulsion. Any of the three components MPL, TDM or CWS may also be used alone or combined 2 by 2. Additionally, adjuvants such as Stimulon (Cambridge Bioscience, Worcester, Mass.) or SAF-1 (Syntex) may be used, as well as adjuvants such as combinations between QS21 and 3-de-O-acetylated monophosphoryl lipid A (WO94/00153), or MF-59 (Chiron), or poly[di (carboxylatophenoxy)phosphazene] based adjuvants (Virus Research Institute), or blockcopolymer based adjuvants such as Optivax (Vaxcel) or Gammalnulin (Anutech), or Gerbu (Gerbu Biotechnik). Furthermore, Complete Freund's Adjuvant (CFA) and Incomplete Freund's Adjuvant (IFA) may be used for non-human applications and research purposes. "A vaccine composition" will further contain excipients and diluents, which are inherently non-toxic and non-therapeutic, such as water, saline, glycerol, ethanol, wetting or emulsifying agents, pH buffering substances, preservatives, and the like. Typically, a vaccine composition is prepared as an injectable, either as a liquid solution or suspension. Solid forms, suitable for solution on, or suspension in, liquid vehicles prior to injection may also be prepared. The preparation may also be emulsified or encapsulated in liposomes for enhancing adjuvant effect. The polypeptides may also be incorporated into Immune Stimulating Complexes together with saponins, for example Quil A (ISCOMS). Vaccine compositions comprise an immunologically effective amount of the polypeptides of the present invention, as well as any other of the above-mentioned components. "Immunologically effective amount" means that the administration of that amount to an individual, either in a single doses or as part of a series, is effective for prevention or treatment. This amount varies depending upon the health and physical condition of the individual to be treated, the taxonomic group of the individual to be treated (e.g. nonhuman primate, primate, etc.), the capacity of the individual's immune system to mount an effective immune response, the degree of protection desired, the formulation of the vaccine, the treating's doctor assessment, the strain of the infecting HCV and other relevant factors. It is expected that the amount will fall in a relatively broad range that can be determined through routine trials. Usually, the amount will vary from 0.01 to 1000 $\mu$g/dose, more particularly from 0.1 to 100 $\mu$g/dose. The vaccine compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents. It should be noted that a vaccine may also be useful for treatment of an individual, in which case it is called a "therapeutic vaccine".

Moreover, the present invention regards a composition comprising a molecule, including antibodies which may be generated by the host itself upon vaccination, which modulates the binding between HCV and a protein as described above, or a functionally equivalent variant or fragment thereof. The term "a molecule which modulates the binding between HCV and a protein as described above, or a functionally equivalent variant or fragment thereof" refers to any molecule derived from the screening method as described above.

In addition, controllable infection of eukaryotic cells by HCV is a prerequisite for studying the binding parameters of HCV to eukaryotic cells. Therefore, the present invention concerns an in vitro infection method of eukaryotic cells for HCV which uses an enriched HCV particle fraction. The term "in vitro infection method" refers to any method allowing a complete replication cycle of a virus in a cell culture based assay system. The term "an enriched HCV particle fraction" refers to HCV particles in solution, in which said HCV particles are separated from non-HCV molecules. The term "enriched" refers to any fraction in which the ratio between said HCV particles and said non-HCV molecules is increased by a factor 10, more preferably by a factor 20, more preferably by a factor 50, more preferably by a factor 100, more preferably by a factor 500, more preferably by a factor $10^3$, and most preferably by a factor $10^4$ compared to the original sample. The term "HCV particles" refers to any complex containing at least HCV RNA and/or proteins, and said complex being able to infect eukaryotic cells.

More specifically, the present invention relates to an in vitro infection method in which the purified HCV particle fraction is obtained by ultra centrifugation of a solution containing said HCV particles. The term "ultra centrifugation of a solution" refers to any centrifugation known to the man skilled in the art and described in eg Maniatis et al. (1982) such as to centrifuging a solution through a cushion of sugar like sucrose or salt like cesium chloride, sodium chloride, or to equilibrium density gradient centrifugation, in which a density gradient is established and said HCV particles are forced to migrate be means of centrifugation to the fraction with an equal density, or by density centrifugation, in which said HCV particles are pelleted because of their density. More specifically, the present invention relates to an in vitro infection method in which body fluid as described above is used as source of HCV particles. More specifically, the present invention relates to an in vitro infection method of Daudi, Molt. HepG2, or any B-, T-, macrophage, hepatocyte or hepatoma cells. In general, the term "cells" refers to any cell, cell type, or cell line which is permissive for infection by HCV particles, HCV-related particles, e.g. HBV, GBV-A, or GBV-B. The term "Daudi cells" refers to eukaryotic cells, which are permissive for infection by HCV particles (ATCC designation CCL213). More specifically, the present invention pertains to an in vitro infection method as described above, in which the purified HCV particle fraction is characterized for its content of E1 and/or E2 proteins, or, of antibodies against E1 and/or E2, or, of LDL, or, of apolipoprotein B, all as described above. The terms "characterized for its content" refer to any method to determine the quantity and/or quality of said HCV particle fraction known to the man skilled in the art, such as ELISA, RIA, PCR, in vitro infection assay, Amplicor (Roche), Monitor (Roche), or any other competitive PCR, branched DNA (Chiron) and as described in the example section of the present invention. The present invention also relates to an in vitro infection method as described above, used for screening for molecules which modulate the binding between HCV and eukaryotic cells, or which interfere with any other step in the replication of HCV and related viruses, all as described above.

In addition, the present invention relates to the use of an in vitro infection method as described above, for diagnosing exposure to or infection by HCV comprising enriched HCV particles as described above, infecting host cells as described above, and determining the multiplicity of infection as described above.

In addition, the present invention pertains to providing isolated E1 and/or E2 peptides of HCV, as defined by SEQ ID NO 1 to 6 (table 4), or any fragment thereof, wherein said sequence binds to annexin V, tubulin and/or apolipoprotein B.

Finally, the present invention will now be illustrated by reference to the following examples which set forth particularly advantageous embodiments. However, it should be noted that these embodiments are illustrative and can not be construed as to restrict the invention in any way.

EXAMPLES

Example 1

In Vitro Infection and Inoculum Characterization

In the replication mechanisms of HCV, one of the first steps is the entry of the virus into the host cell. This entry, using purified inocula, was studied by monitoring the presence and secretion of HCV upon inoculation of T cells.

Two inocula for infection were prepared from two different human donor sera by sedimentation centrifugation through a sucrose cushion. Therefore, a number of sera obtained from HCV-positive blood donors were screened for HCV-RNA by PCR, envelope antibody titres and genotype 1b (this allows to perform comparative studies, since all recombinant proteins, peptides and monoclonal antibodies used for these experiments are also derived from or directed to a 1b sequence). Two sera from genotype 1b with high RNA titres and low antibody titres were retained for inoculum preparation. The purification applied to these sera is a rough separation of the majority of the serum components from the virus which is pelleted by ultra centrifugation through a sucrose cushion according to the following protocol: Human serum or plasma containing HCV particles was diluted by addition of 5 volumes TEN (mM TRIS pH 8.0, mM EDTA, mM NaCl) and 34 ml of the diluted serum or plasma was placed in a polyallomer tube suitable for ultra centrifugation in a SW27 rotor (Beckman). A cushion of 2 ml 20% sucrose in TEN pH 8.0 was carefully pipetted underneath the diluted serum. Ultra centrifugation conditions were 28,000 rpm for 5.5 hrs at 4° C. in an SW27 rotor. After centrifugation, the supernatant including the sucrose cushion was discarded and 400 µl ice-cold TEN pH 8.0 was added to the HCV-enriched pellet which was left to gently solubilize overnight at 4° C. The solubilized pellets were pooled, divided in 150-µl aliquots, stored at −70° C., and assayed quantitatively for HCV RNA by means of competitive PCR, anti-envelope (E1 and E2) immunoglobulin, E1/E2 protein, and LDL content.

The LDL content was measured using a sandwich ELISA based on commercially available antibodies. The monoclonal 2B4 (Cappel, Organon Teknika, Turnhout, Belgium) was used as capturing antibody and a goat-anti-human LDL polyclonal serum (Sigma) was used for detection. Purified human LDL (Cappel) was used as a quantitative standard.

Figure 1:
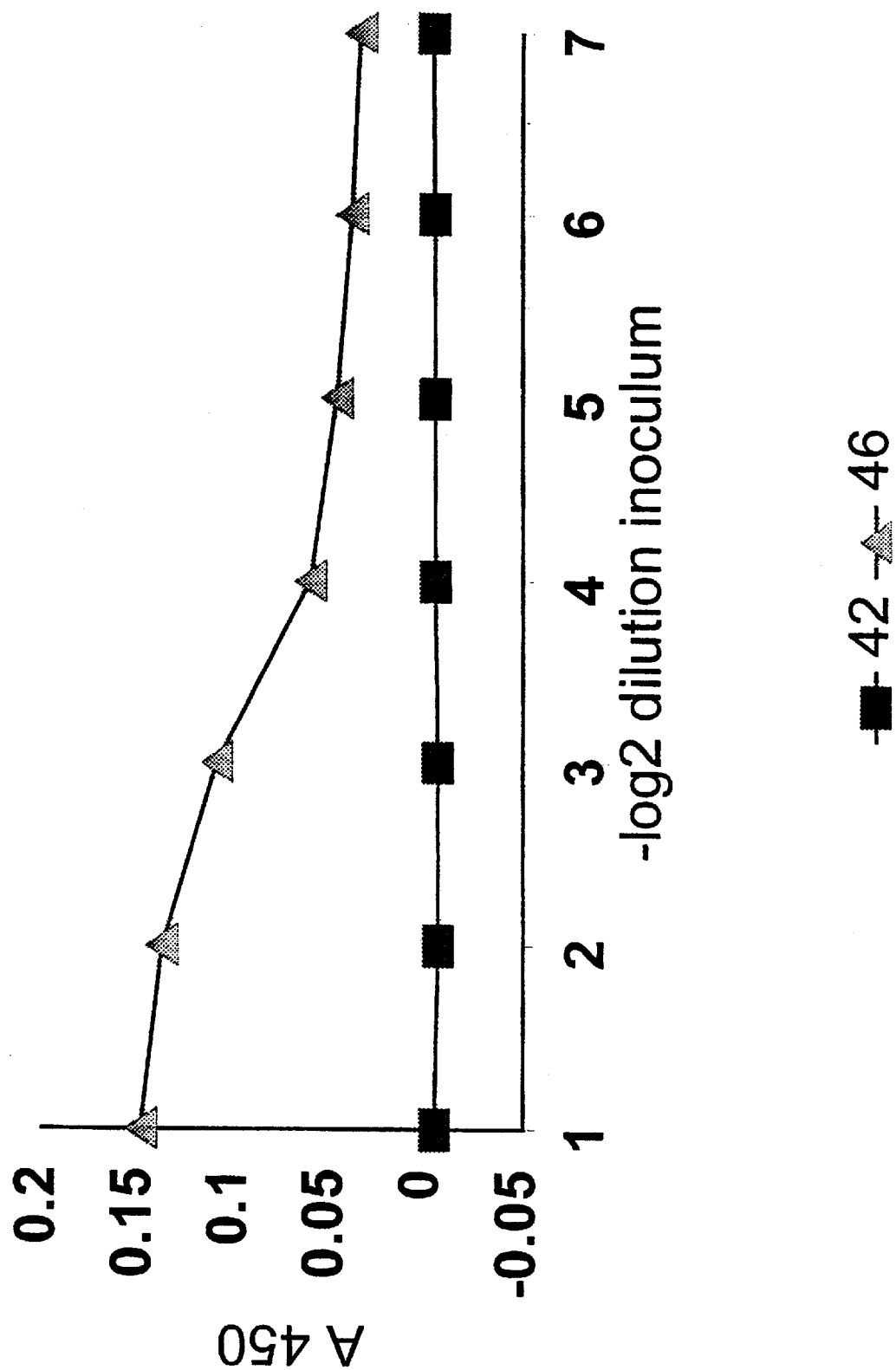

The anti-E1/E2 titre was determined by ELISA. E1 and E2 were adsorbed to microtiterplates and after incubation with a serial dilution of the samples, bound IgG was detected by means of an rabbit-anti-human IgG/Fc (Dako, Roskilde, Denmark) labelled with peroxidase. E1/E2 proteins itself were determined by adsorbing a serial dilution of the inoculum preparations to microtiterplates and detecting the envelope proteins using a mixture of in house (i.e. which can be obtained from the inventors at Innogenetics N.V., Gent, Belgium) monoclonal antibodies directed against E1 and E2. Visualization was performed using an coat-anti-mouse IgG/Fc (Jackson) labelled with peroxidase (for result see also FIG. 1).

The PCR titre was determined on a serial dilution of the sample. More specifically, an RT-PCR was used amplifying the 5'UTR of HCV such as described in Stuyver et al., 1996. The genotype was determined using INNO-Lipa HCV II (Innogenetics, Gent, Belgium).

The inocula were also characterized in an in vitro infection assay. Therefore cells were infected with an multiplicity of infection (m.o.i.) of 10. A fixed m.o.i. was used for the infection in order to be able to compare the different inocula. The amount of inoculum needed to obtain a m.o.i. of 10 was calculated based on the assumption that 1 PCR unit equals 100 RNA molecules (=100 HCV virions). This infection experiment was performed using Daudi cell line (ATCC CCL 213) which was already reported to be permissive for HCV infection (Shimizu et al., 1996). This infection was performed according to the following protocol: 1) suspend $5.10^5$ cells in serum free RPMI medium at a concentration of $10^6$ cells/ml; 2) add inoculum to obtain m.o.i. of 10; 3) add serum free RPMI medium to obtain a total volume of 1 ml; 4) incubate the infection at 37° C. for 16 h; 5) wash cells 3 times with RPMI medium containing serum; 6) suspend cells and seed cells in a 96-well plate ($5 * 10^4$ cells per well in a volume of 200 µl); 7) sample (=harvest one well completely) cells and supernatant daily; 8) divide cell cultures when necessary. The presence of virus in both supernatant and cells was determined by PCR as described above.

Table 1 shows that the presence of both LDL and antibodies against E1/E2 in the semi-purified inocula (denoted serum 42 and 46, "after") was reduced 200–2000 times compared to the serum from which they were derived (denoted serum 42 and 46, "before"). The final antibody content, LDL content and PCR titre were similar for both inocula. The presence of E1/E2 protein was only detectable in inoculum 46. Table 2 demonstrates that, although an equal amount of HCV-RNA was used for infection, only the inoculum with a detectable level of E1/E2 protein (inoculum 46) produced detectable progeny virus (i.e. HCV-RNA could be detected). HCV-RNA could be detected, both in cells and culture medium, during a 10–12 day period for inoculum 46. Inoculum 42 on the other hand only produced a transient and weak (only nested PCR positive) signal during the first 4 days after infection.

From these data, it can be concluded that high RNA titres do not necessarily reflect high amounts of infective virus. The preparation of inocula containing detectable amounts of E1/E2 protein is crucial in order to obtain an infection of host cells. The latter observation indicates that viral entry of HCV is mediated via E1 and /or E2 and that these proteins can interact directly with the cell membrane of the host. However, it can not be excluded that viral uptake may be mediated by LDL since the inoculum was not free of LDL.

Example 2

Interaction of E1 or E2 with LDL

We determined binding of recombinant E1 and E2 (expressed and produced in mammalian cells as truncated proteins: E1s aa 192–326 and E2s aa 384–673 as described in Maertens et al. (1994) and de Martynoff et al. (1996) to solid LDL. LDL (Cappel) wad adsorbed to microtiterplates, binding of envelope proteins was performed using biotinylated proteins (in addition to E1s an E1 derivative from which a putative internal hydrophobic domain was deleted was tested: E1s Δbam=aa 192–340 with deletion of aa 264–287). Binding is detected by means of streptavidin labelled with peroxidase.

Figure 2A:
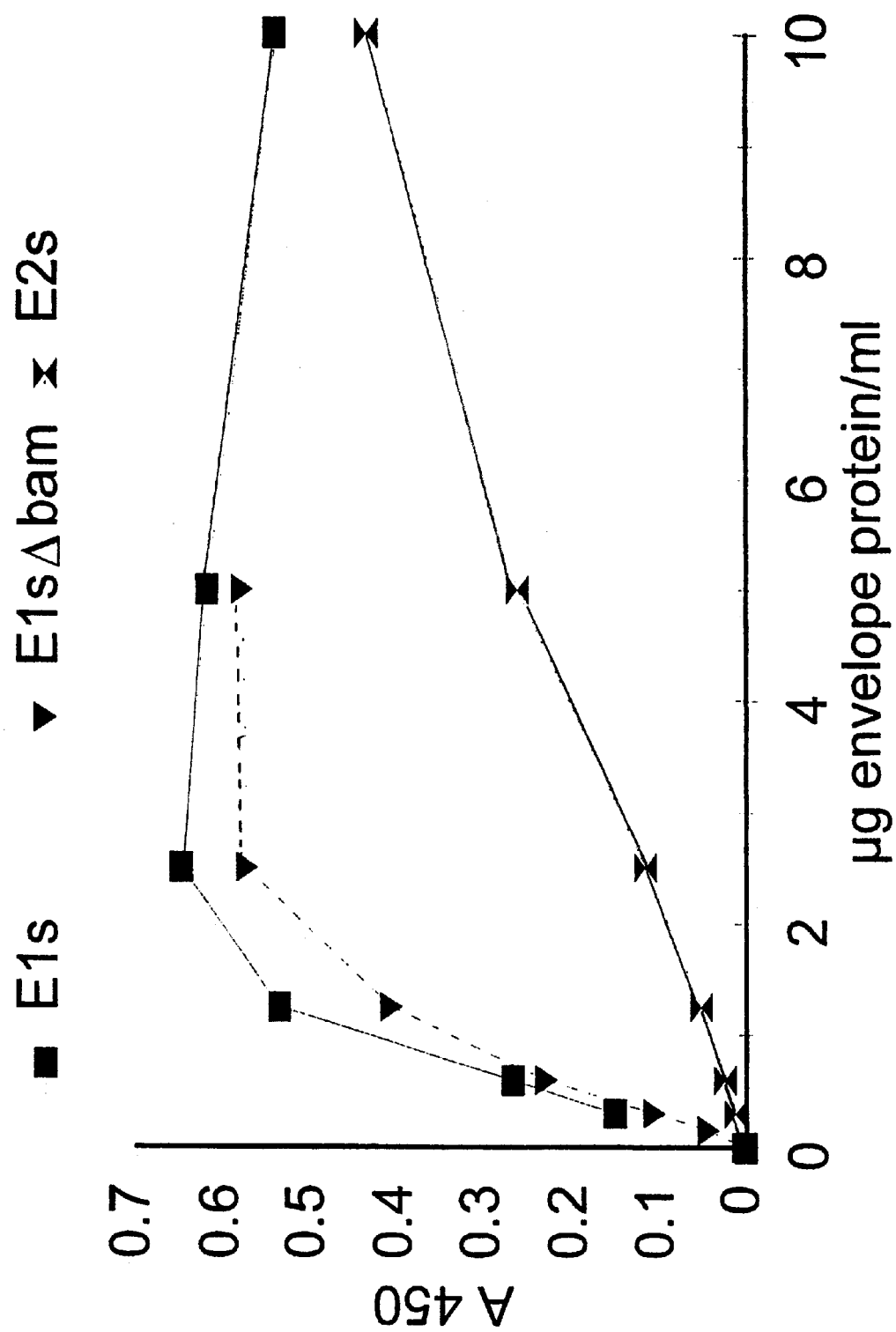
Figure 2B:
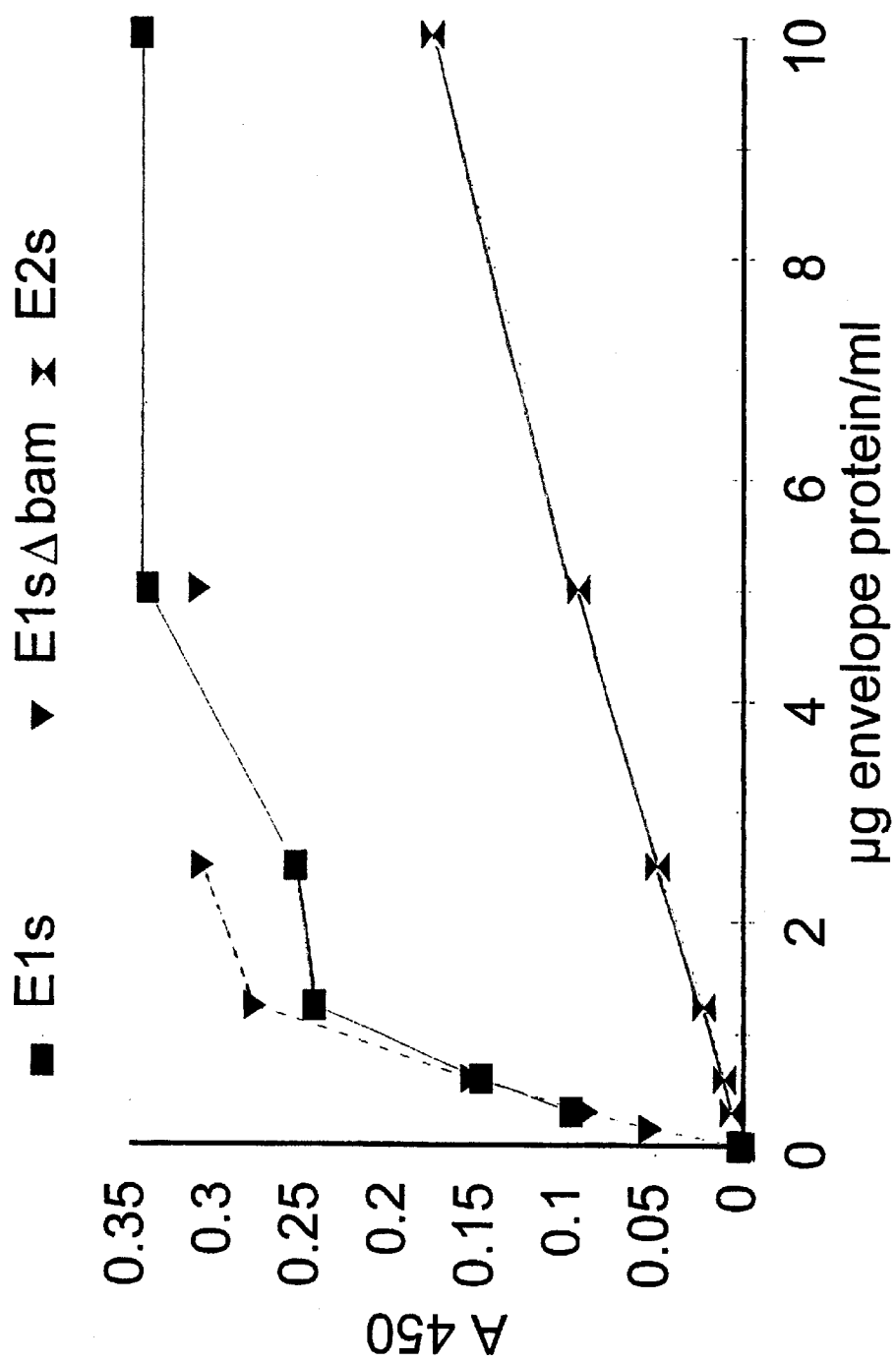

FIG. 2A shows that only E1 and E1s Δbam bound LDL in a concentration-dependent and saturable way. The latter binding is irrespective of the E1 genotype (types 1b, 4 and 5 were tested, data not shown). To further characterize this interaction, we determined binding of the major protein component of LDL, i.e. apolipoprotein B, to E1. FIG. 2B demonstrates that, in a similar way as for LDL (see above), only E1 and E1 sΔbam bound apolipoprotein B (also purchased from Cappel) in a concentration dependent and saturable way. Surprisingly the binding curves observed for E1 in the binding experiment with LDL and apolipoprotein B are nearly identical. This proves that the interaction of E1 with LDL is solely mediated through apolipoprotein B and not to any lipid or other protein component present in LDL. The finding that the putative internal hydrophobic domain of E1 is not involved in the binding with LDL, indicated already that the interaction with LDL is not based on hydrophobic associations such as lipid binding.

The interaction of E1 with apolipoprotein B may contribute to viral entry via the LDL-receptor, but our current results indicate that this does not involve direct binding of E1 with the LDL-receptor, as claimed by Agnello et al. (1997). On the other hand, binding of HCV via E1 to LDL may result in a viral particle shielded from immune attack. Any intervention in this binding could influence the viral life cycle and can be used for therapeutic intervention in the disease.

Example 3

Binding of E1 and E2 to Cells

Recombinant E1s and E2s proteins were produced separately using an eukaryotic expression by vaccinia virus (de Martynoff et al., 1996). Binding of these proteins to several human cells lines from haematopoietic origin was demonstrated (Table 3). Briefly $5 * 10^5$ cells were allowed to bind biotinylated E1 or E2 (concentration range 0–20 µg) at 4° C., excess protein was removed by centrifugation and bound E1 or E2 was detected by means of streptavidin labelled with FITC. This binding was analysed in a flow cytometer (Beckton Dickinson, FACS). FIG. 3 shows that this binding is concentration dependent and saturable both for E1 (a–e) as well as for E2 (f–j). Table 3 demonstrates that the binding is species specific since such a binding could not be demonstrated to B- and T cells from murine origin.

Example 4

Identification of Intracellular E1 and E2 Binding Proteins

Total cell extracts were prepared from Daudi cells. Briefly, cells are lysed in the presence of 1% CHAPS detergent using a Dounce homogenizer, cell debris is removed by centrifugation and the resulting supernatant is further referred to as cell extract. The extracts were affinity-adsorbed on E1 and E2 affinity columns in order to capture E1 or E2 binding proteins. Briefly these columns were prepared as follows: streptavidin was bound to agarose mini-leak according to the manufacturer's protocol (Biozym), after which E1 or E2 was allowed to bind to the streptavidin. After the cell extract has passed the column, the column was further washed using 0.05% CHAPS, to remove nonspecifically bound proteins. Elution of bound proteins was performed as a three step elution. The first elution was performed at pH 11.5, a second one at pH 2.5, and an elution combining high pH (11.5) and a strong detergent (1%

Empigen). Only the last elution step resulted in the recovery of a single protein of 55 kDa binding to both E1 and E2. The SDS-PAGE from the first alkaline elution revealed that this step served as an additional washing since a whole smear of proteins was recovered. The acidic elution was not able to elute any protein from the columns (data not shown).

Figure 4:

A single extract from $10^9$ cells was passed over an E2 column, the column was washed and eluted as described above and the fraction obtained from the third elution was analysed on SDS-PAGE. Staining of the gel was performed with Coomassie Brilliant Blue (CBB) and revealed a 55 kDa band (FIG. 4). The additional band appearing at 70 kDa is a nonspecific binding protein, since this band is also recovered from columns to which no E2 was bound (data not shown). Since the 55 kDa band could be visualized with CBB it was judged that this band contained sufficient material for sequencing.

The 55 kDa band was eluted from the SDS-PAGE, digested with trypsin (Rosenfeld et al., 1992) and the resulting peptides separated by HPLC (C4 Vydac column, 1.0×250 mm). All peaks containing sequencable material resulted in identification of either tubulin-alpha or tubulin-beta. By way of example the sequences of two peaks resulting in the identification in tubulin-alpha and tubulin-beta are presented below (amino acids allowing discrimination between tubulin-alpha and -beta are underlined):

```
peak 63        AVFVDLEPTVIDE
               (identified as tubulin-alpha aa
               65-77) (SEQ ID NO: 7)

tubulin-alpha  AVFVDLEPTVIDE (SEQ ID NO: 8)

tubulin-beta   AVLVDLEGTMDSV (SEQ ID NO: 9)

peak 58        XXXYFVEXIXNXV
               (identified as tubulin-beta aa
               337-349 (SEQ ID NO: 10)

tubulin-beta   NSSYFVEWIPNNV (SEO ID NO: 11)

tubulin-alpha  RTIQFVDWCPTGF (SEQ ID NO: 12).
```

Figure 5:
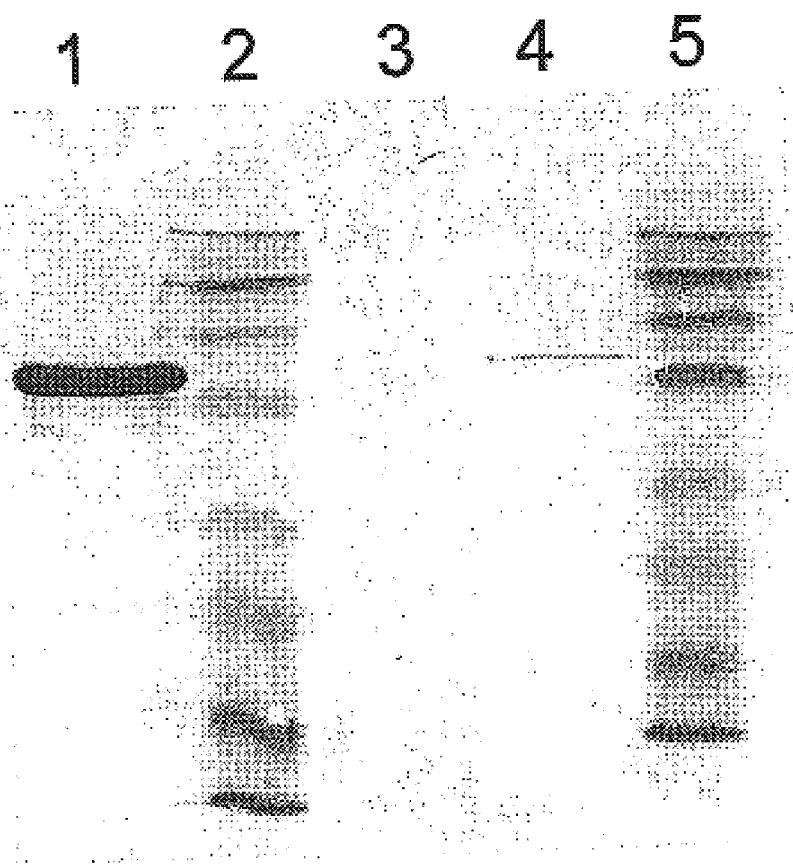

FIG. 5 shows that, by using specific monoclonal antibodies against tubulin (Sigma), the E1 binding protein of 55 kDa (from the third elution) was confirmed to contain tubulin.

Furthermore the specificity of this interaction was confirmed by immunoprecipitation, 2 µg biotinylated E1 or E2 were incubated for 1 h at 37° C. with 2 µg tubulin in 50 µl $TBS_{Mg,Ca}$+0.05% CHAPS ($TBS_{Mg,Ca}$ is: 10 mM TRIS-HCl, 150 mM NaCl, 1 mM $CaCl_2$, 1 mM $MgCl_2$, pH 7.5). An 1/500 dilution of monoclonal anti-α-tubulin and anti-β-tubulin (Sigma) in 50 µl $TBS_{Mg,Ca}$+0.05% CHAPS was added (1 h, 37° C.). To precipitate the complex, 100 µl of blocked (0.01% BSA) protein A glass beads (BioPROCESSING) were added (1 h, RT, mixing). After washing the beads with $TBS_{Mg,Ca}$+0.05% tween-20, the bound complex was eluted with 50 µl sample buffer (containing 3% SDS and 100 mM DTT) at 95° C., 5 min. The samples were analysed with Western blot and E1 or E2 were detected by means of streptavidin labelled with alkaline phosphatase.

Figure 7A:
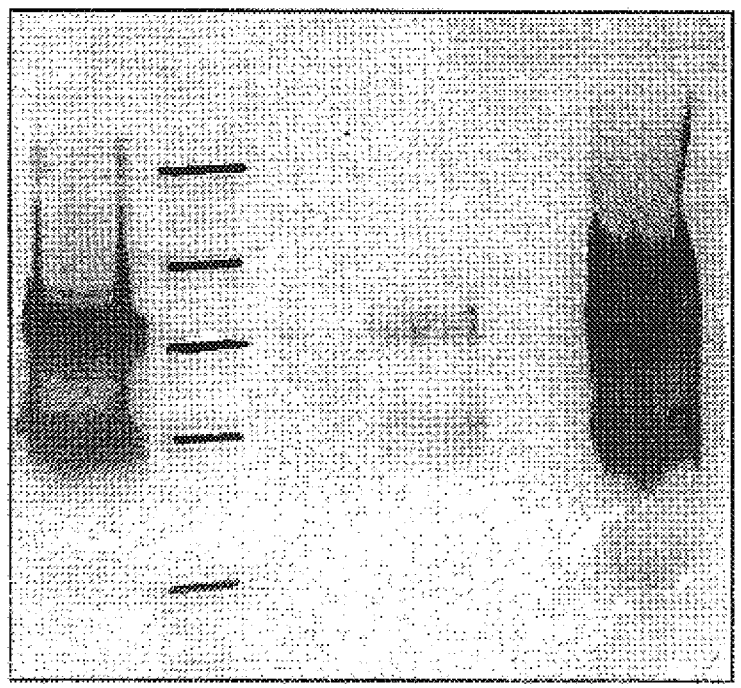
Figure 7B:
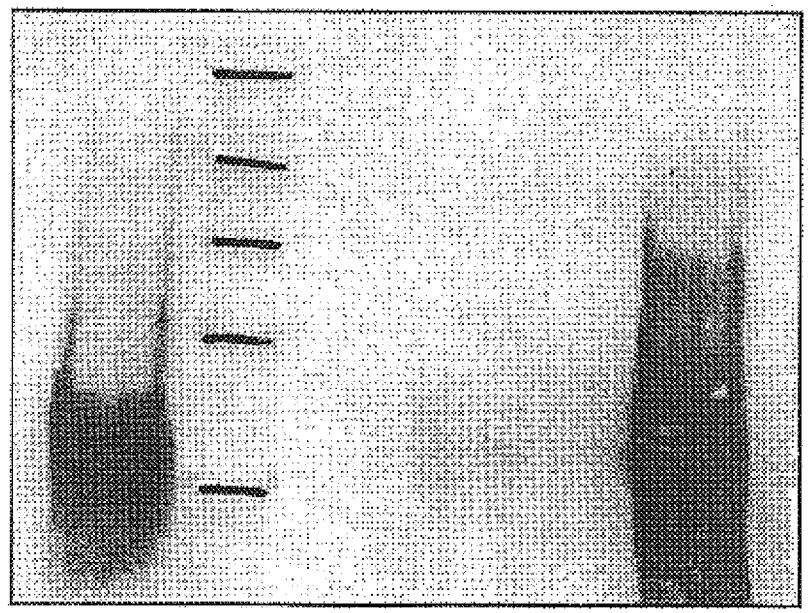

The Western blots (FIG. 7) revealed the clear presence of E1 and E2 only after precipitation using monoclonal antibody against tubulin in the presence of tubulin while the control experiments (precipitation in the absence of tubulin) show virtually no E1 and E2.

Example 5

Interaction of E1 or E2 with Annexins

FIGS. 6A and B demonstrate that annexin V binds to both E1 and E2. FIG. 6 further shows that the interaction of annexin V with E1 and E2 was mapped to the amino acids 307–326 of E1 (peptide C4V6, but with exclusion of aa 327–340 since these aa are not part of the recombinant E1s) and 413–467 (peptides C1 and C2) of E2. Both interaction sites are relatively well conserved regions of E1 and E2 and therefore it may be concluded that the interaction of annexin V to E1 and E2 is not limited to the genotype 1b but may also occur with other HCV genotypes. Moreover, and since annexin V is a member of the annexin family which covers 13 known members, also other members of this family may interact with the HCV envelope proteins.

The experiments described in FIG. 6 were performed as follows: both peptides and recombinant envelope proteins were biotinylated and as such adsorbed to microtiterplates coated with streptavidin. These plates were further incubated with A-V labelled with peroxidase. Binding of A-V to streptavidin was subtracted and the remaining absorbance was plotted. For E1 the binding to the region C4V6 is striking and comparable to the binding observed with E1s itself, since this peptide only overlaps with E1s in the region 307–325, this region is considered as representing the A-V binding site on E1. For E2 a similar result was obtained, binding of A-V was most obvious for peptides C1 and C2, therefore these peptides are considered to cover the most important region of E2 involved in A-V binding. Such peptides (see list below) are potential vaccine candidates since the antibodies induced by these peptides will interfere directly with the viral life cycle. The induction of such antibodies may result in extremely potent vaccines since it may be expected that they will be cross-protective for all genotypes if one assumes that the processes targeted are used in the life cycle of all HCV genotypes.

| peptides | aa region |
|---|---|
| V1V2 | 192–226 |
| V2V3 | 212–244 |
| V3V4 | 230–263 |
| V4V5 | 240–263/288–303 |
| V5C4 | 288–327 |
| C4V6 | 307–340 |
| E1s | 192–325 |
| HVR I | 384–415 |
| HVR1/C1 | 395–428 |
| C1 | 413–447 |
| C2 | 430–467 |
| HVRII | 466–487 |
| C3 | 480–513 |
| C4 | 500–530 |
| 13/17 | 523–566 |
| C5 | 561–590 |
| 23/27 | 578–627 |
| C6 | 621–648 |
| C7 | 641–673 |
| E2s | 384–673 |

LIST OF REFERENCES

Alberts B., Bray D., Lewis J., Raff M., Roberts K., Watson J. D. Molecular Biology of the Cell, 1983, Garland, New York.

Agnello V., Abel G., Zhang Q X, Elfahal M., Knight G B, Low density lipoprotein receptor mediated endocytosis of hepatitis C virus: a potential mechanism for infection of hepatocytes. Triennial meeting of viral hepatitis, Rome 1996, B122.

Agnello V., Abel G., Zhang Q. X., Elfahal M., Knight G. B. The low density lipoprotein receptor is a receptor for the hepatitis C virus, Kvoto meeting 1997.

Atherton, Shepard (1989) Solid phase peptide synthesis, IRL Press, Oxford.

Bianchi R, Giambanco I, Ceccarelli P, Pula G, Donato R (1992) Membrane-bound annexin V isoforms (CaBP33 and CaBP37) and annexin VI in bovine tissues behave like integral membrane proteins. FEBS Letters 296:158–162.

Current protocols in immunology, Eds Coligan J., Kruisbeek A., Margulis D., Shevach E. And Strober W. Wiley Interscience, 1992.

de Martynoff G., Venneman A., Maertens G. Analysis of post-translational modifications of HCV structural proteins by using the vaccinia virus expression systems. Proceedings of the 'IX Triennial international symposium on viral hepatitis and liver disease', Rome 1996, in press.

Deleersnyder V., Pillez A., Wychowski C., Blight K., Xu J., Hahn Y. S., Rice C. M., Dubuisson J. Formation of native hepatitis C virus glycoprotein complexes. J. Virol. 1997: 71: 697–704.

Farci P., Shimoda A., Wong D., Cabezon T., De Gionnis D., Strazzera A., Shimizu Y., Shapiro M., Alter H. J., Purcell R. H. Prevention of hepatitis C virus infection in chimpanzees by hyperimmune serum against the hyper variable region 1 of the envelope 2 protein. PNAS 1996: 93: 15394–15399.

Grundmann U, Abel K, Bohn H, Lobermnann H, Lottspeich F, Kupper H (1988) Characterization of cDNA encoding human placental anticoagulant protein (PP4) homology with the lipocortin family. Proc Natl Acad Sci USA 85:3708–3712.

Haigler H. Schlaepher D, Burgess W, Haigler H (1987) Characterization of lipocortin I and an immunologically related 33-kD protein as epidermal growth factor receptor (human substrate and phopholipase A2 inhibitors). J Biol Chem 262:6921–6930.

Hammonds T. R., Denyer S. P., Jackson D. E., Irving W. L. Studies to show that with podophyllotoxin the early replicative stages of herpes simplex virus type 1 depend upon functional cytoplasmic microtubules. J. Med. Microbiol, 1996: 167–72.

Hertogs K, Leenders W P J, Depla E, De Bruin W C C, Meheus L, Raymackers J, Moshage H, Yap S H (1993) Endonexin II, present on human liver plasma membranes, is a specific binding protein of small hepatitis B virus (HBV) envelope protein. Virology 197:549–557.

Hertogs K, Depla E, Crabbe T, De Bruin W, Leenders W, Moshage H, Yap S H (1994) Spontaneous development of anti-hepatitis B virus envelope (anti-idiotypic) antibodies in animals immunized with human liver endonexin II or with the F(ab'), fragment of anti-human liver endonexin II immunoglobulin G: evidence for a receptor-ligand-like relationship between small hepatitis B surface antigen and endonexin II. J Virol 68:1516–1521.

Houbenweyl (1974) Methode der organischen chemie. vol. 15, I & II (ed. Wunch E), Thieme, Stuttgart.

Klee B (1988) $Ca^{2+}$-dependent phospholipid -and membrane-binding proteins. Biochemistry Maertens G., Ducatteeuw A., Stuyver L., Vandeponseele P., Venneman A., Wyseur A., Bosman F., Heijtink R. & de Martynoff G. (1994) Low prevalence of anti-E1 antibodies reactive to recombinant type 1b E1 envelope protein in type 2, 3, and 4 sera, but high prevalence in subtypes 1a and 1b. In: Viral Hepatitis and Liver Disease, Tokyo, 1993 (Eds. Nishioka K., Suzuki H., Mishiro S. & Oda T.), pp 314–316, Springer Verlag Tokyo.

Maertens G. And Stuyver L. Genotypes and genetic variation of hepatitis C virus. In: The molecular medicine of viral hepatitis. Ed: Harrison T. J. and Zuckerman A. J. 1997

Major M. E. and Feinstone S. M. The molecular virology of hepatitis C. Hepatology 1997:25:1527–1538.

Maniatis T. Fritsch E, Sambrook J (1982) Molecular cloning: a laboratory manual, Cold Spring Harbor Laboratory Press, Cold Spring Harbor, N.Y.

McLean B. G. Zupan J., Zambryski P. C. Tobacco mosaic virus movement protein associates with the cytoskeleton in tobacco cells, Plant Cell, 1995: 2101–2114.

Melki R., Gaudin Y., Blondel D. Interaction between tubulin and the viral matrix protein of vesicular stomatitis virus: possible implications in the viral cytopathic effect. Virology 1994: 339–347.

Monazahian, M., Mueller, A., Hornei. B. and Thomssen, R. (1995) Binding of LDL and VLDL to recombinant E1-proteins of HCV. Observatioin of an insertion of a human RNA sequence in the E2 region. C84, 3th Int. Symp. Hepatitis C virus and related viruses. Brisbane, Australia.

Pepinsky R, Tizard R, Mattaliano J et al. (1998) Five distinct calcium and phospholipid binding proteins share homology with lipocortin I. J Biol Chem 263:10799–10811.

Rojas E, Pollard H, Haigler H, Parra C, Burns L (1990) Calcium-activated human endonexin II forms calcium channels across acidic bilayer membranes. J Biol Chem 265:21207–21215.

Rosa D., Campagnoli S., Moretto C., Guenzi E., Cousens L., Chin M;, Dong C., Weiner A.J., Lau J. Y. N., Choo Q. L., Chien D., Pileri P., Houghton M., Abrignani S. A quantitative test to estimate neutralizing antibodies to the hepatitis C virus: cytofluorimetric assessment of envelope glycoprotein 2 binding to target cells. PNAS 1996: 93: 1759–1763.

Rosenfeld J., Capdevielle J., Guillemot J. C., Ferrara P. In-gel digestion of proteins for internal sequencing analysis after one- or two-dimensional gel electrophoresis. Anal. Biochem. 1992: 203: 173–179.

Scanu A. M. Plasma Apolipoproteins: Gene structure, Function, and Variants pp 141–190, in: The plasma proteins, 2nd edition, Vol. V. Eds Putnam, F. W. 1987, Academic Press Inc. London, UK.

Shimizu Y., Hijikata M., Iwamoto A., Alter H. J., Purcell R. H., Yoshikura H. Neutralizing antibodies against hepatitis C virus and the emergence of neutralization escape mutant viruses. J. Virol. 1994: 68: 1494–1500.

Shimizu Y., Feinstone S., Kohara M., Purcell R., Yoshilkura H. Hepatitis C virus: detection of intracellular virus particles by electron microscopy. Hepatology 1996:23:205–209.

Stuyver L.. Wyseur A., Van Arnhem W., Hernandez F., Maertens G. Second-generation line probe assay for hepatitis C virus genotyping, J. Clin. Microbiol. 1996:34:2259–2266.

Takagi T., Iwama M., Seta K., Kanda T., Tsukamoto T., Tominaga S., Mizumoto K. Positive and negative factors for Sendai virus transcription and their organ distribution in rat. Arch. Virol. 1996:141:1623–1635.

Thomssen R., Bonk S., Profke C., Heermann K. H., Köchel H. G., Uy A. Association of hepatitis C virus in human sera with beta-lipoprotein. Med. Microbiol. Immunol. 1992:181:293–300.

Thomssen R., Bonk S., Thiele A. Density heterogeneities of hepatitis C virus in human sera due to the binding of beta-lipoproteins and immunoglobulin. Med. Microbiol. Immunol. 1992:182:329–334.

Walker JH, Boustead C, Brown R, Koster J, Middleton C (1990) Tissue and subcellular distribution of endonexin, a calcium-dependent phospholipid-binding protein. Biochem Soc Trans 18:1235–1236.

Yi M., Nakarnoto Y., Kaneko S., Yamashita T., Murakaami S. Delineation of regions important for heteromeric association of Hepatitis C virus E1 and E2. Virol. 1997a:231:119–129.

Yi M., Kaneko S., Yu D. Y., Murakami S. Hepatitis C virus envelope proteins bind lactoferrin. J. Virol. 1997b:71:5997–6002

Zaks W. Creutz C (1990) Evaluation of the annexins as potential mediators of membrane fusion in exocytosis. J. Bioener Biomembr 22:97–119.

Zibert A., Schreier E., Roggendorf M. Antibodies in human sera specific to hyper variable region 1 of hepatitis C virus can block viral attachment. Virol. 1995:208:653–661.

TABLE 1

| | serum 42 | | serum 46 | |
|---|---|---|---|---|
| | before | after | before | after |
| LDL (µg/ml) | 87 | 1.5 | 180 | 1.25 |
| anti E1/E2 (titre) | 181 | 8 | 256 | 11 |
| E1/E2 (see figure) | nd | neg | nd | pos |
| PCR titre | nd | $5 \times 10^5$ | nd | $1 \times 10^6$ |
| genotype | 1b | | 1b | |

TABLE 2

| Inoculum incubation day | 42 16th CF | SN | 46 16th CF | SN |
|---|---|---|---|---|
| 0 | ++ | − | ++ | − |
| 3 | + | − | ++ | ++ |
| 4 | + | − | ++ | − |
| 5 | − | − | ++ | ++ |
| 6 | − | − | ++ | ++ |
| 7 | − | − | ++ | − |
| 10 | + | − | ++ | ++ |
| 11 | − | − | − | − |
| 12 | − | − | ++ | − |
| 13 | − | − | − | − |
| 14 | − | − | − | − |

TABLE 3

| Type | Origin | Name | E1 | E2 |
|---|---|---|---|---|
| monocyte | human | HL 60 | − | ++ |
| | | U937 | + | ++ |
| | mouse | WEHI | − | − |
| B-cell | human | (Daudi) | + | ++ |
| | | Ramos | + | + |
| | | RPMI 1788 | + | ++ |
| | | SKW 6.4 | ++ | ++ |
| | | CESS | (+) | ++ |
| | mouse | Raw8.1 | nd | − |
| T-cell | human | CCRF CEM | ++ | ++ |
| | | Molt-4 | + | + |
| | mouse | LBRM 33 | nd | − |

TABLE 4

| SEQ ID | HCV Type | Position | |
|---|---|---|---|
| 5 | E2 | 384–673 | HTRVSGGAAASNTRGLVSLFSPGSAQKIQLVNTNGSWHINRTALNCNDSLQT GFFAALFYKHKFNSSGCPERLASCRSIDKFAQGWGPLTYTEPNSSDQRPYCW HYAPRPCGIVPASQVCGPVYCFTPSPVVVGTTDRFGVPTYNWGANDSDVLIL NNTRPPRGNWFGCTWMNGTGFTKTCGGPPCNIGGAGNNTLTCPTDCFRKHPE ATYARCGSGPWLTPRCMVHYPYRLWHYPCTVNFTIFKVRMYVGGVEHRFGAA CNWTRGERCDLEDRDRSELSPLLLSTTEWQ |
| 6 | E2 | 413–467 | LVNTNGSWHINRTALNCNDSLQTGFFAALFYKHKFNSSGCPERLASCRSIDK FAQ |
| 3 | E1 | 192–326 | YEVRNVSGIYHVTNDCSNSSIVYEAADMIMHTPGCVPCVRENNSSRCWVALT PTLAARNASVPTTTIRRHVDLLVGAAAFCSAMYVGDLCGSVFLVSQLFTISP RRHETVQDCNCSIYPGHITGHRMAWDMMMNW |
| 2 | E1 | 307–326 | SIYPGHITGHRMAWDMMMNW |
| 1 | E1 | 192–263 | YEVRNVSGIYHVTNDCSNSSIVYEAADMIMHTPGCVPCVRENNSSRCWVALT PTLAARNASVPTTTIRRHVD |
| 4 | E1 | 288–326 | sQLFTISPRRHETVQDCNCSIYPGHITGHRMAWDMMMNw |

What is claimed is:

1. A method of screening for molecules which modulate the binding between HCV and human apolipoprotein B or a functional fragment of human apolipoprotein B, comprising:

(i) contacting an HCV E1 envelope protein or a composition comprising an HCV E1 envelope protein with said molecule, and a human apolipoprotein B or a functional fragment of a human apolipoprotein B, under conditions whereby said molecule compete with the binding of said envelope protein to said human apolipoprotein B or said functional fragment of a human apolipoprotein B; and (ii) determining the amount of HCV E1 envelope protein bound to the human apolipoprotein B or the functional fragment, whereby said amount correlates to the molecule being a modulator of the binding between HCV and the human apolipoprotein B or the functional fragment.

2. A method of screening for molecules which modulate the binding between HCV and human apolipoprotein B or a functional fragment of human apolipoprotein B, comprising:

(i) contacting a predetermined amount of HCV E1 envelope protein or a composition comprising a predetermined amount of HCV E1 envelope protein with said molecule, and a human apolipoprotein B or a functional fragment of a human apolipoprotein B, under conditions whereby said molecule compete with the binding of said envelope protein to said human apolipoprotein B or said functional fragment of a human apolipoprotein B; and (ii) determining the amount of HCV E1 envelope protein bound to the human apolipoprotein B or the functional fragment, whereby said amount correlates to the molecule being a modulator of the binding between HCV and the human apolipoprotein B or the functional fragment.

3. A method of any of claims 1–2, wherein said molecule enhances binding between a HCV E1 envelope protein and a human apolipoprotein B or a functional-fragment of a human apolipoprotein B.

4. A method of any of claims 1–2, wherein said molecule decreases binding between a HCV E1 envelope protein and a human apolipoprotein B or a functional-fragment of a human apolipoprotein B.

5. The method according to any of claims 1 to 2, wherein said HCV E1 envelope protein consists of the region spanning amino acids 192–263, consists of the region spanning amino acids 288–326, consists of E1s Δbam or is represented by SEQ ID NOs: 1, 3 or 4 or a fragment of SEQ ID NOs: 1, 3, or 4.

6. A method of screening for molecules which modulated the binding between HCV and human apolipoprotein B or a functional fragment of human apolipoprotein B, comprising:

(i) providing a complex of HCV bound to the human apolipoprotein B or the functional fragment, (ii) contacting a molecule suspected of being a modulator of the binding between HCV and a human apolipoprotein B or a functional fragment of human apolipoprotein B, with the complex of step (i), (iii) determining changes in binding in said complex, whereby a change in binding correlates to the molecule being a modulator of the binding between HCV and the human apolipoprotein B or the functional fragment.

7. A method of screening for molecules which modulate the binding between HCV and human apolipoprotein B or a functional fragment of human apolipoprotein B, comprising:

(i) providing a complex of HCV from a sample of body fluid, bound to the human apolipoprotein B or the functional fragment, (ii) contacting a molecule suspected of being a modulator of the binding between HCV and a human apolipoprotein B or a functional fragment of human apolipoprotein B, with the complex of step (i), (iii) determining changes in binding in said complex, whereby a change in binding correlates to the molecule being a modulator of the binding between HCV and the human apolipoprotein B or the functional fragment.

8. A method of any of claims 6–7, wherein said molecule enhances binding between HCV and a human apolipoprotein B or a functional fragment of a human apolipoprotein B.

9. A method of any of claims 6–7, wherein said molecule decreases binding between HCV and a human apolipoprotein B or a functional fragment of a human apolipoprotein B.

10. A method according to any of claims 6–7, wherein said HCV comprises at least one HCV envelope E1 protein.

11. The method according to claim 10, wherein said HCV E1 envelope protein consists of the region spanning amino acids 192–263, consists of the region spanning amino acids 288–326, consists of E1s Δbam or is represented by SEQ ID NOs: 1, 3 or 4 or a fragment of SEQ ID NOs: 1, 3, or 4.

12. A method of screening for molecules according to any of claim 1, 2, 6 or 7 wherein said molecule is selected from the group consisting of an antibody and a peptide.

13. The method of claim 12, wherein said molecule is selected from the group consisting of a human antibody, a monoclonal antibody, an E1-peptide and a apolipoprotein B peptide.

* * * * *

UNITED STATES PATENT AND TRADEMARK OFFICE
CERTIFICATE OF CORRECTION

PATENT NO.     : 6,670,114 B1
DATED          : December 30, 2003
INVENTOR(S)    : Maertens et al.

It is certified that error appears in the above-identified patent and that said Letters Patent is hereby corrected as shown below:

Column 6,
Line 22, delete "binding2" and insert therefor -- binding --.
Line 34, delete "and I" and insert therefor -- and I --.
Line 35, delete "5." and insert therefore -- 5, --.

Column 8,
Line 4, delete "bounds" and insert therefor -- bonds --.

Column 10,
Line 54, delete "inhibiting)" and insert therefor -- inhibiting)) --.

Column 11,
Line 67, delete "RIB1" and insert therfor -- RIBI --.

Column 12,
Line 13, delete "Gammalnulin" and insert therefor -- Gammainulin --.

Column 13,
Line 36, delete "Molt." and insert therfor -- Molt, --.

Column 14,
Line 65, delete "coat" and insert therefor -- goat --.

Column 18,
Line 49, Table: delete "466-487" and insert therefor -- 460-487 --.

Column 19,
Line 3, delete "Kvoto" and insert therefor -- Kyoto --.
Line 60, add -- 27, 6645-6653 --.

UNITED STATES PATENT AND TRADEMARK OFFICE
CERTIFICATE OF CORRECTION

PATENT NO. : 6,670,114 B1
DATED : December 30, 2003
INVENTOR(S) : Maertens et al.

It is certified that error appears in the above-identified patent and that said Letters Patent is hereby corrected as shown below:

Column 21,
Line 74, delete "Nakarnoto" and insert therefor -- Nakamoto --.

Column 30,
Line 41, delete "modulated" and insert therefor -- modulate --.

Signed and Sealed this

Seventeenth Day of August, 2004

JON W. DUDAS
*Acting Director of the United States Patent and Trademark Office*

SEQUENCE LISTING

<160> NUMBER OF SEQ ID NOS: 12

<210> SEQ ID NO 1
<211> LENGTH: 19
<212> TYPE: PRT
<213> ORGANISM: Hepatitis C virus

<400> SEQUENCE: 1

Ser Ile Tyr Pro Gly His Ile Thr Gly His Arg Met Ala Trp Asp Met
 1               5                  10                  15

Met Met Asn

<210> SEQ ID NO 2
<211> LENGTH: 135
<212> TYPE: PRT
<213> ORGANISM: Hepatitis C virus

<400> SEQUENCE: 2

```
Tyr Glu Val Arg Asn Val Ser Gly Ile Tyr His Val Thr Asn Asp Cys
 1               5                  10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp
    130                 135
```

<210> SEQ ID NO 3
<211> LENGTH: 39
<212> TYPE: PRT
<213> ORGANISM: Hepatitis C virus

<400> SEQUENCE: 3

```
Ser Gln Leu Phe Thr Ile Ser Pro Arg Arg His Glu Thr Val Gln Asp
 1               5                  10                  15

Cys Asn Cys Ser Ile Tyr Pro Gly His Ile Thr Gly His Arg Met Ala
            20                  25                  30

Trp Asp Met Met Met Asn Trp
        35
```

<210> SEQ ID NO 4
<211> LENGTH: 290
<212> TYPE: PRT
<213> ORGANISM: Hepatitis C virus

<400> SEQUENCE: 4

```
His Thr Arg Val Ser Gly Gly Ala Ala Ala Ser Asn Thr Arg Gly Leu
 1               5                  10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95
```

```
Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
            115                 120                 125

Ser Pro Val Val Val Gly Thr Thr Asp Arg Phe Gly Val Pro Thr Tyr
            130                 135                 140

Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
            195                 200                 205

Ala Thr Tyr Ala Arg Cys Gly Ser Gly Pro Trp Leu Thr Pro Arg Cys
            210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Gly Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Glu
            275                 280                 285

Trp Gln
    290

<210> SEQ ID NO 5
<211> LENGTH: 55
<212> TYPE: PRT
<213> ORGANISM: Hepatitis C virus

<400> SEQUENCE: 5

Leu Val Asn Thr Asn Gly Ser Trp His Ile Asn Arg Thr Ala Leu Asn
1               5                   10                  15

Cys Asn Asp Ser Leu Gln Thr Gly Phe Phe Ala Ala Leu Phe Tyr Lys
            20                  25                  30

His Lys Phe Asn Ser Ser Gly Cys Pro Glu Arg Leu Ala Ser Cys Arg
        35                  40                  45

Ser Ile Asp Lys Phe Ala Gln
    50                  55

<210> SEQ ID NO 6
<211> LENGTH: 72
<212> TYPE: PRT
<213> ORGANISM: Hepatitis C virus

<400> SEQUENCE: 6

Tyr Glu Val Arg Asn Val Ser Gly Ile Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60
```

```
Thr Thr Ile Arg Arg His Val Asp
 65                 70

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: peak 63

<400> SEQUENCE: 7

Ala Val Phe Val Asp Leu Glu Pro Thr Val Ile Asp Glu
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: tubulin-
      alpha

<400> SEQUENCE: 8

Ala Val Phe Val Asp Leu Glu Pro Thr Val Ile Asp Glu
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: ubulin-beta

<400> SEQUENCE: 9

Ala Val Leu Val Asp Leu Glu Gly Thr Met Asp Ser Val
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: peak 58
<220> FEATURE:
<221> NAME/KEY: SITE
<222> LOCATION: (1)
<223> OTHER INFORMATION: any amino acid
<220> FEATURE:
<221> NAME/KEY: SITE
<222> LOCATION: (2)
<223> OTHER INFORMATION: any amino acid
<220> FEATURE:
<221> NAME/KEY: SITE
<222> LOCATION: (3)
<223> OTHER INFORMATION: any amino acid
<220> FEATURE:
<221> NAME/KEY: SITE
<222> LOCATION: (8)
<223> OTHER INFORMATION: any amino acid
<220> FEATURE:
<221> NAME/KEY: SITE
<222> LOCATION: (10)
<223> OTHER INFORMATION: any amino acid
<220> FEATURE:
<221> NAME/KEY: SITE
<222> LOCATION: (12)
<223> OTHER INFORMATION: any amino acid

<400> SEQUENCE: 10

Xaa Xaa Xaa Tyr Phe Val Glu Xaa Ile Xaa Asn Xaa Val
```

-continued

```
<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: tubulin -
      beta

<400> SEQUENCE: 11

Asn Ser Ser Tyr Phe Val Glu Trp Ile Pro Asn Asn Val
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: tubulin-
      alpha

<400> SEQUENCE: 12

Arg Thr Ile Gln Phe Val Asp Trp Cys Pro Thr Gly Phe
 1               5                  10
```